United States Patent [19]
Swain et al.

[11] Patent Number: 5,840,307
[45] Date of Patent: Nov. 24, 1998

[54] HAPTEN-CARRIER CONJUGATES FOR USE IN DRUG-ABUSE THERAPY AND METHODS FOR PREPARATION

[75] Inventors: Philip A. Swain, Brighton; Victoria Carol Schad, Cambridge; Julia Lea Greenstein, West Newton; Mark Adrian Exley, Brookline; Barbara Saxton Fox, Wayland; Stephen P. Powers, Waltham; Malcolm L. Gefter, Lincoln, all of Mass.

[73] Assignee: ImmuLogic Pharmacuetical Corp., Waltham, Mass.

[21] Appl. No.: 457,206

[22] Filed: Jun. 1, 1995

Related U.S. Application Data

[62] Division of Ser. No. 414,971, Mar. 31, 1995.

[51] Int. Cl.$^6$ .......................... A61K 39/385; A61K 39/00; A61K 39/395; C07P 451/02
[52] U.S. Cl. .................................. 424/193.1; 424/140.1; 424/175.1; 546/130
[58] Field of Search ............................. 424/193.1, 140.1, 424/175.1; 546/130

[56] References Cited

U.S. PATENT DOCUMENTS

| | | | |
|---|---|---|---|
| 4,197,237 | 4/1980 | Leute ........................................ | 260/112 |
| 4,235,864 | 11/1980 | Kaul et al. .................................. | 424/1 |
| 4,375,414 | 3/1983 | Stranievitz . | |
| 4,620,977 | 11/1986 | Strahilevitz . | |
| 4,666,837 | 5/1987 | Harford . | |
| 4,791,067 | 12/1988 | Sheiman . | |
| 4,813,924 | 3/1989 | Strahilevitz . | |
| 4,834,973 | 5/1989 | Strahilevitz . | |
| 5,019,384 | 5/1991 | Gefter . | |
| 5,037,645 | 8/1991 | Strahilevitz . | |
| 5,256,409 | 10/1993 | Blincko ................................... | 424/484 |
| 5,268,276 | 12/1993 | Holmgren . | |
| 5,283,066 | 2/1994 | Liu et al. ................................ | 424/858 |

FOREIGN PATENT DOCUMENTS

| | | |
|---|---|---|
| 0 613 899 A2 | 7/1993 | European Pat. Off. . |
| WO92/03163 | 3/1992 | WIPO . |
| WO93/12111 | 6/1993 | WIPO . |
| WO95/07992 | 3/1995 | WIPO . |
| 9323076 | 9/1995 | WIPO . |

OTHER PUBLICATIONS

Ambre, et al., "A Kinetic Model of Benzoylechonine Disposition after Cocaine Administration in Humans", *Journal of Analytical Toxicology*, vol. 15, 1991, 17–20.

Berkower, "Synthetic T Cell Epitope Peptides Used for Desensitization: Theoretical and Clinical Considerations", Paul–Ehrlich–Institut, Sep. 7–10, 1993.

Bonese, "Changes in heroin self-administration of a rhesus monkey after morphine immunization", *Nature*, vol. 252, Dec. 1974.

Gallacher, "A potential vaccine for cocaine abuse prophylaxis?", *Immunopharm.*, vol. 27, 1994, 79–81.

Holmgren, et al., "Stretehies for the induction of Immune Responses at Mucosal Surfaces . . . ", Am. J. Trop. Med. Hyg., 1994, pp. 42–54.

Inaba, "Cocaine: Pharmacokinetics and biotransformation in man", SFBS Symposium on Frontiers in Cocaine Research, Quebec, Canada, Jun. 15, 1988, pp. 1154–1157.

Jatlow, "Cocaine: Analysis, Pharmacokinetics, and Metobolic Disposition", The Yale Journal of Biology and Medicine, vol. 61, 1988, pp. 105–113.

Jindal, et al., "Mass Spectrometric Studies of Cocaine Disposition in Animals . . . ", Journal of Pharmaceutical Sciences, vol. 78, No. 12, 1989, pp. 1009–1014.

Kantak, et al., "Acute and multiple injection effects of magnesium on resonding maintained by Cocaine, . . . ", Pharm. Biochem. and Behavior, vol. 41, 1992, pp. 415–423.

Manganaro, et al., "Oral Immunization: Turning Fantasy into Reality", Int. Arch. Immunol., vol. 103, 1994, pp. 223–233.

Stok, et al., "Conversion of orally induced supression of the mucosal immune response to ovalbumin into stimulation by conjugating . . . ", Vaccine, vol. 12, 1994, No. 6, pp. 521–526.

Slos, et al., "Recombinant cholera toxin B subunit in Escherichia coli: high–level secretion, purification and characterization", Protein Expresion and Purification, vol. 5, 1994, pp. 518–526.

Witkin, "Pharmacotherapy of Cocaine Abuse: Preclinical Development", Neurosci. and Biobehav. Reviews, vol. 18, No. 1, 1994, pp. 121–142.

Jones–Witters and Witters, Drugs and Society — A Biological Perspective, Wadsworth Health Sciences Division, 1983, Wadsworth, Inc., Belmont, California 94002, pp. 142–147.

Wu, et al., "Comparison of systemic and mucosal priming for mucosal immune responses to a bacterial protein antigen . . . ", Vaccine, 1994, vol. 12, No. 3, pp. 215–222.

Currueru, R. et al., (1993) *Society for Neuroscience* 754.4 (Abstract).

Bagasra et al. Immunopharmacology (1992) vol. 23 pp. 173–179.

*Primary Examiner*—James C. Housel
*Assistant Examiner*—Jennifer Shaver
*Attorney, Agent, or Firm*—Christopher A. Klein; Stacey L. Channing; Anne I. Craig

[57] ABSTRACT

Hapten-carrier conjugates capable of eliciting anti hapten antibodies in vivo by administering, in a therapeutic composition, are disclosed. Anti-hapten antibodies elicited compete with free hapten upon subsequent challenge of a vaccinated individual. Methods of preparing said conjugates and therapeutic compositions are also disclosed. Where the hapten is a drug of abuse, a therapeutic composition containing the hapten-carrier conjugate is particularly useful in the treatment of drug addiction, more particularly, cocaine addiction. Passive immunization using antibodies raised against conjugates of the instant invention is also disclosed. The therapeutic composition is suitable for co-therapy with other conventional drugs.

3 Claims, 21 Drawing Sheets

(-)-COCAINE

| | | |
|---|---|---|
| CJ 0 | Q | Q = H, OH, CH$_2$, halogen, COOH, carrier protein, modified carrier protein |
| CJ 1 | (CH$_2$)nQ | Q = H, COOH, halogen, 2-nitro-4-sulfophenyl ester, N-oxysuccinimidyl ester, carrier protein, modified carrier protein, CJ 1.2 |
| CJ 1.1 | CO$_2$Q | Q = H, CH$_3$ |
| CJ 1.2 | COQ | Q = H, halogen, 1-oxy-2-nitro-4-sulfophenyl, N-oxysuccinimidyl, N-maleimidyl, carrier protein, CJ 10 |
| CJ 2 | OCO(CH$_2$)nQ | Q = COOH, halogen, 2-nitro-4-sulfophenyl ester, N-oxysuccinimidyl ester, carrier protein, modified carrier protein |
| CJ 2.1 | OCOCH=Q | Q = H |
| CJ 2.2 | OCOCH(O)CH$_2$ | |
| CJ 2.3 | OCO(CH$_2$)nCH(O)CH$_2$ | |
| CJ 3 | CO(CH$_2$)nCOQ | Q = H, OH, halogen, 1-oxy-2-nitro-4-sulfophenyl, N-oxysuccinimidyl, N-maleimidyl, carrier protein, CJ 10 |
| CJ 3.1 | CO(CH$_2$)nCNQ | Q = OCH$_3$ or carrier protein |
| CJ 4 | OCO(CH$_2$)nCOQ | Q = H, OH, halogen, 1-oxy-2-nitro-4-sulfophenyl, N-oxysuccinimidyl, N-maleimidyl, carrier protein, CJ 10 |
| CJ 4.1 | CO(CH$_2$)nCNQ | Q = OCH$_3$ or carrier protein |
| CJ 5 | CH$_2$OCO(CH$_2$)nCOQ | Q = H, OH, halogen, 1-oxy-2-nitro-4-sulfophenyl, N-oxysuccinimidyl, N-maleimidyl, carrier protein, CJ 10 |
| CJ 5.1 | CO(CH$_2$)nCNQ | Q = OCH$_3$ or carrier protein |
| CJ 6 | CONH(CH$_2$)nQ | Q = H, COOH, halogen, 2-nitro-4-sulfophenyl ester, N-oxysuccinimidyl ester, carrier protein, modified carrier protein |
| CJ 7 | Y(CH$_2$)nQ | Y = S, O, NH; Q = halogen, COOH, carrier protein, modified carrier protein |
| CJ 7.1 | CH$_2$Y(CH$_2$)nQ | Y = S, O, NH; Q = halogen, COOH, carrier protein, modified carrier protein |
| CJ 8 | OCOCH(OH)CH$_2$Q | Q = carrier protein, modified carrier protein |
| CJ 8.1 | OCO(CH$_2$)nCH(OH)CH$_2$Q | Q = carrier protein, modified carrier protein |
| CJ 9 | OCOC$_6$H$_5$ | |
| CJ 9.1 | OCOC$_6$HZ | Z = longer chain CJ groups |

Fig. 2a

CJ 10   N(C)OCH₂CHQ'    Q' = MODIFIED PROTEIN

ALTERNATE REPRESENTATION FOR SELECTED BRANCHES:

CJ 2.2              CJ 2.3

CJ 9                CJ 10

| | A | B | C | D | E | F |
|---|---|---|---|---|---|---|
| PS-2 | CJ 1.1 where Q = CH$_3$ | CJ 2 where Q = halogen, modified carrier protein and n=1 | CJ 0 where Q = H | CJ 0 where Q = H | CJ 0 where Q = H | CJ 1 where Q = H, n = 1 |
| PS-3 | " | CJ 0 where Q = modified carrier protein | " | " | " | " |
| PS-4 | " | CJ 4 where Q = carrier protein and n = 1 | " | " | " | " |
| PS-5 | " | CJ 9 | " | " | " | CJ 3 where Q = carrier protein and n = 2 |
| PS-6 | CJ 5 where Q = carrier protein and n = 2 | " | " | " | " | CJ 1 where Q = H and n = 1 |
| PS-9 | CJ 1.2 where Q = carrier protein | " | " | " | " | " |
| PS-10 | CJ 6 where Q = H or CJ 1.1 where Q = CH$_3$ | CJ 2 where Q = halogen | CJ 0 where Q = H | CJ 0 where Q = H | CJ 0 where Q = H | CJ 1 where Q = H, n = 1 |
| PS-11 | " | CJ 2 where Q = modified carrier protein | " | " | " | " |
| PS-12 | " | CJ 2.1 | " | " | " | " |
| PS-13 | " | CJ 2 Q = carrier protein, modified carrier protein and n = 2 | " | " | " | " |
| PS-14 | " | CJ 2.2 | | | | |
| PS-15 | " | CJ 8 | | | | |
| PS-16 | " | CJ 2.3 | | | | |
| PS-17 | " | CJ 8.1 | | | | |
| PS-18 | " | CJ 4 | | | | |
| PS-19 | CJ 6 where Q = H or CJ 1.1 where Q = CH$_3$ | CJ 1 where Q = COOH, halogen, 2-nitro-4-sulfophenyl ester, n-oxysuccinimidyl ester, carrier protein, modified carrier | CJ 0 where Q = H | CJ 0 where Q = H | CJ 0 where Q = H | CJ 1 where Q = H, n = 1 |

Fig. 3b-1

| | A | B | C | D | E | F |
|---|---|---|---|---|---|---|
| PS-20 | " | CJ 7 | " | " | " | " |
| PS-21 | " | CJ 9 | " | " | " | CJ 3 |
| PS-22 | " | " | " | " | " | CJ 1 where Q = CJ 1.2 |
| PS-23 | CJ 5 | " | " | " | " | CJ 1 where Q = H |
| PS-24 | CJ 7.1 | " | " | " | " | " |
| PS-25 | CJ 7 | " | " | " | " | " |
| PS-26 | CJ 1.2 | " | " | " | " | " |
| PS-27 | CJ 6 where Q = H, or CJ 1.1 where Q = CH$_3$ | CJ 9 | CJ 2 | CJ 0 where Q = H | CJ 0 where Q = H | CJ 1 where Q = H, n = 1 |
| PS-28 | " | " | CJ 1 where Q = COOH, halogen, 2-nitro-4-sulfophenyl ester, N-oxysuccinimi-dyl ester, carrier protein, modified carrier protein, CJ 1.2 | " | " | " |
| PS-29 | " | " | CJ 2.2 | " | " | " |
| PS-30 | " | " | CJ 8 | " | " | " |
| PS-31 | " | " | CJ 2.3 | " | " | " |
| PS-32 | " | " | CJ 8.1 | " | " | " |
| PS-33 | " | " | CJ 4 | " | " | " |
| PS-34 | " | " | CJ 5 | " | " | " |
| PS-35 | CJ 6 where Q = H, or CJ 1.1 where Q = CH$_3$ | CJ 9 | CJ 0 where Q = H | CJ 2 | CJ 0 where Q = H | CJ 1 where Q = H, n = 1 |

Fig. 3b-2

| | A | B | C | D | E | F |
|---|---|---|---|---|---|---|
| PS-36 | " | " | " | CJ 1 where Q = COOH, halogen, 2-nitro-4-sulfophenyl ester, N-oxysuccinimidyl ester, carrier protein, modified carrier protein, CJ 1.2 | " | " |
| PS-37 | " | " | " | CJ 2.2 | " | " |
| PS-38 | " | " | " | CJ 8 | " | " |
| PS-39 | " | " | " | CJ 2.3 | " | " |
| PS-40 | " | " | " | CJ 8.1 | | |
| PS-41 | " | | | CJ 4 | | |
| PS-42 | " | | | CJ 5 | | |
| PS-43 | CJ 6 where Q = H, or CJ 1.1 where Q = CH$_3$ | CJ 9 | CJ 0 where Q = H | CJ 0 where Q = H | CJ 2 | CJ 1 where Q = H, n=1 |
| PS-44 | " | | " | | CJ 1 where Q = COOH, 2-nitro-4-sulfophenyl ester, N-oxysuccinimidyl ester, carrier protein, modified carrier protein, CJ 1.2 | " |
| PS-45 | " | " | " | " | CJ 2.2 | " |
| PS-46 | " | " | " | " | CJ 8 | " |
| PS-47 | " | " | " | " | CJ 2.3 | " |
| PS-48 | " | " | " | " | CJ 8.1 | " |
| PS-49 | " | " | " | " | CJ 4 | " |
| PS-50 | " | " | " | " | CJ 5 | " |

Fig. 3b-3

|  | A | B | C | D | E | F |
|---|---|---|---|---|---|---|
| COCAINE | CJ 1.1 where Q = CH$_3$ | CJ 9 | CJ 0 where Q = H | CJ 0 where Q = H | CJ 0 where Q = H | CJ 1 where Q = H, n = 1 |
| ECGONINE METHYL ESTER | " | CJ 10 where Q = OH | " | " | " | " |
| NORCOCAINE | " | CJ 9 | " | " | " | CJ 0 where Q = H |
| BENZOYL ECGONINE | CJ 0 where Q = COOH | " | " | " | " | CJ 1 where Q = H, n = 1 |

Fig. 4

HAPTEN-CARRIER CONJUGATES FOR USE IN DRUG-ABUSE THERAPY AND METHODS FOR PREPARATION

This application is a divisional of U.S. Ser. No. 08/414,971, filed on Mar. 31, 1995, and which is hereby incorporated herein by reference.

The prevalence of drug use and abuse worldwide, especially in the United States, has reached epidemic levels. There are a plethora of drugs, both legal and illegal, the abuse of which have become serious public policy issues affecting all strata of society with its obvious medical and social consequences. Some users live in an extremely high risk population associated with poverty and illegal activity. Other users who might class themselves as recreational users are at risk due to (a) properties of the drug(s) which make them addictive, (b) a predisposition of the user to become a heavy user or (c) a combination of factors including personal circumstances, hardship, environment and accessibility. Adequate treatment of drug abuse, including polydrug abuse, requires innovative and creative programs of intervention.

An especially problematic drug is cocaine, an alkaloid derived from the leaves of the coca plant (*Erythroxylon coca*). In the United States alone, there currently are more than 5 million regular cocaine users of whom at least 600,000 are classified as severely addicted (1,2). Within this population, a significant number of addicts actively are seeking therapy. For example, in 1990, 380,000 people sought medical treatment for cocaine addiction and the number is increasing. At that time, it was estimated that 100,000 emergency room admissions per year involve cocaine use. The cumulative effects of cocaine-associated violent crime, loss in individual productivity, illness, and death is an international problem.

The lack of effective therapies for the treatment of cocaine addiction strongly suggests that novel approaches must be developed. Additional factors contributing to the lack of successful treatment programs is that patterns of cocaine abuse have varied with time. In an article entitled "1994 Chemical Approaches to the Treatment of Cocaine Abuse", (F. Ivy Carroll et al., *Pharm. News*, Vol. 1, No. 2,1994 Chemical Approaches to the Treatment Cocaine Abuse.), F. Ivy Carroll reports that since the mid-1980's, intravenous and nasal dosing of the hydrochloride salt (coke, snow, blow) and smoking of cocaine free-base (crack) have become common routes of administration, producing euphoria and psychomotor stimulation which last 30–60 minutes. Unlike some other abused drugs, cocaine can be taken in binges lasting for several hours. This behavior leads to addiction, and in some cases, to toxic consequences (F. Ivy Carroll et al., *Pharm. News*, supra.).

There are only very limited treatments for drugs of abuse and no effective long term treatments for cocaine addiction. Treatments include, but are not limited to, counseling coupled with the administration of drugs that act as antagonists at the opioid receptors or drugs that try to reduce the craving associated with drug addiction. One approach to treatment is detoxification. Even temporary remissions with attendant physical, social and psychological improvements are preferable to the continuation or progressive acceleration of abuse and its related adverse medical and interpersonal consequences (*Harrision's Principle of Internal Medicine* Vol. 2, 12th Ed.,Chap. 372, p 2157–8, Wilson et al., 1991 McGraw-Hill.) More specifically, pharmacological approaches to the treatment of cocaine abuse generally involve the use of anti-depressant drugs, such as desipramine or fluoxetine which may help manage the psychological aspects of withdrawal but, in general, do not directly affect the physiology of cocaine. Further, their effectiveness varies widely (Brooke, D. et al (1992), *Drug Alcohol Depend.*, 31:37–43). In some studies, desipramine reduced self-administration (20,31,32) but abstinence rate following treatment did not exceed 70% (4). There has also been the use of drugs which potentiate dopaminergic transmission, such as bromocriptine, but the benefits of such drugs are limited in part by toxicity (Taylor W. A., et al, (1990) West. J . Med., 152:573–577). New drugs aimed at replacing methadone for opioid addiction, such as buprenorphine, have also been used based on cross-interference with the dopaminergic system, however only limited clinical study information is available (Fudula, P. J., et al. (1991) *NIDA Research Monograph*, 105:587–588). Buprenorphine has been reported to decrease cocaine self-administration (29–31); however, cocaine abstinence rates following treatment generally do not exceed 50% (3,5).

Present therapies used to treat cocaine addicts have at least four major limitations leading to a very high rate of recidivism. First, and perhaps most fundamentally, the contributing neurochemical events in cocaine abuse and addiction are complex (Carroll, et al, (1994) supra.). As a result, single acting neuropharmacological approaches, such as inhibition of dopamine uptake, do not appear to be sufficient to overcome addiction. Second, the drugs currently used in cocaine addiction treatments have significant side-effects themselves, limiting their utility. Third, drug therapy compliance is problematic among this patient population. Current therapies can require frequent visits to a health care provider and/or self-administration of drugs designed to cure the addict of his habit. Because many of these drugs prevent the euphoria associated with cocaine, there is a strong disincentive to taking the drug. (Carroll, et al, (1994) supra.; Gastfried, D. R., et al., (1994) *College on Problems of Drug Dependence Meeting Abstracts*; Kosten, T. R., et al (1993), Problems of Drug Dependence, *NIDA Res. Monogr.* 85; Schottenfeld, R. S. et al (1993), Problems of Drug Dependence, *NIDA Res. Monogr.* 311.) Fourth, because of the complex chemistries involved in pharmacological therapies, many of them may be incompatible with other therapies currently in use or in clinical trials.

Experimental diagnostic approaches and therapies have been suggested in the literature which have yet to be practiced. For example, vaccination as a therapeutic approach for drug addiction has been described previously in principle. Bonese et al. investigated changes in heroin self-administration by a rhesus monkey after immunization against morphine (Bonese, K. F. et al., (1974) *Nature* 252:708–710). Bagasra et al. investigated using cocaine-KLH vaccination as a means to prevent addiction. He immunized rats with cocaine-KLH conjugate which did raise some anti-cocaine antibodies. However, the results were disappointing because none of the animals immunized with the cocaine-KLH conjugate exhibited resistance to cocaine exposure as measured in a hot plate model (Bagasra. O. et al., (1992) *Immunopharmacol.* 23:173–179.). Obviously, if a conjugate is to be effective in a therapeutic regimen, it must possess be capable of raising antibodies that can recognize free cocaine circulating in vivo and that are of the appropriate affinity, avidity.

Passive administration of monoclonal antibodies to treat drug abuse has been previously described (see Killian, A. et al, (1978)). Effects of passive immunization against morphine on heroin self-administration,*Pharmacol. Biochem. & Behavior*, 9:347–352; Pentel, P. R., et al. (1991), Redistribution of Tricyclic Antidepressants, *Drug Metabolism& Dispositions*, 19:24–28). In this approach, pre-formed antibodies to selected drugs are passively administered to animals. While these data provide a demonstration of the feasibility of immunological approaches to addiction therapy, passive immunization as a long term human therapeutic strategy suffers from a number of major drawbacks. First, passively administered antibodies are cleared relatively rapidly from the circulation. The half life of a given antibody in vivo is between 2.5 and 23 days, depending on the isotype. Thus, when the antibodies are passively administered, rather than induced by immunization, only short term effectiveness can be achieved. Second, antibodies that can be used for passive therapy must be obtained either from an immunized animal (polyclonal antisera) or as a monoclonal antibody. In either case, these preparations will be seen as foreign proteins by the patient, and there will be a rapid immune response to the foreign antibodies. This immune response will neutralize the passively administered antibody, blocking its effectiveness and drastically reducing the time of subsequent protection. In addition, readministration of the same antibody will become problematic, due to the potential induction of a-hypersensitivity response.

Another immunological approach to drug addiction has been to use a catalytic antibody which is capable of aiding hydrolysis of the cocaine molecule within the patient (Landry, D. W., et al.,(1993) Antibody-catalyzed degradation of cocaine, *Science*, 259:1899–1901). The catalytic antibody is generated by immunization of an experimental animal with a transition state analog of cocaine linked to a carrier protein; a monoclonal antibody is then selected that has the desired catalytic activity. Although this approach is attractive theoretically, it also suffers from some serious problems. Catalytic antibodies must be administered passively and thus suffer from all of the drawbacks of passive antibody therapy. Active immunization to generate a catalytic antibody is not feasible, because enzymatic activity is rare among antibodies raised against transition state analogs, and activity does not appear to be detectable in polyclonal preparations. In addition, the general esterase-like activity of such catalytic antibodies and the uncontrolled nature of the active immune response in genetically diverse individuals makes them potentially toxic molecules, particularly when they are being produced within a human patient.

Yugawa et al, EP 0 613 899 A2 filed Jul. 16, 1993 (the "Matsushita application") have suggested the use of cocaine-protein conjugate using a cocaine derivative for use in raising antibodies for the detection of cocaine or cocaine derivatives in a blood sample.

Syva patents describe conjugates to raise cocaine antibodies for immunoassays. Disclosed are conjugates to BSA using diazonium salts derived from benzoyl ecognine and cocaine. Conjugates are made using para-imino ester derivatives of cocaine and norcocaine to conjugate a carrier. U.S. Pat. No. 3,888,866, U.S. Pat. No. 4,123,431 and U.S. Pat. No. 4,129,237.

Biosite (WO9312111) discloses conjugates of cocaine using the para-position of the phenyl ring of various cocaine derivatives increasing stability to hydrolysis by introducing an amide bond.

Strahilevitz, in a series of related patents (U.S. Pat. No. 4,620,977; U.S. Pat. No. 4,813,924; U.S. Pat. No. 4,834,973; and U.S. Pat. No. 5,037,645) disclose using protein conjugates of endogenous substances and drugs for treatment of diseases, preventing dependence on psychoactive haptens, as well as for use in immunoassays, immunodialysis and immunoadsorption.

Due to these limitations, no effective therapy for drug addiction, especially, cocaine addiction, has been developed. Thus, it is apparent that there is a need to develop a long term treatment approach to drug addiction, in particular cocaine addiction, which does not depend totally on the addicted individual for compliance and self-administration. The present invention overcomes the above mentioned drawbacks and provides methods for treating drug abuse. Using therapeutic compositions, in particular hapten-carrier conjugates, the present invention elicits an immune response in the form of anti-drug antibodies within the addict which upon subsequent exposure to the drug in a vaccinated individual neutralizes the drug so the expected pharmacological effects are diminished, if not eliminated.

Therefore it is an object of this invention to provide a hapten-carrier conjugate with variable haptenization properties such that the anti-hapten antibodies are optimized.

It is another object of this invention to treat drug addiction by immunizing humans addicted to drugs, especially cocaine, by administering therapeutic composition containing at least one hapten-carrier conjugate.

It is still other object of this invention to prepare conjugates with maximal haptenation.

It is another object of this invention to optimize the titer, affinity, and specificity of the anti-drug, and in particular anti-cocaine, antibody response in diverse patient populations.

It is another object of this invention to provide a high stringency physiological screen for efficacy of antibodies raised by selected conjugates.

It is another object of this invention to provide forms of cocaine as a hapten that are capable of being conjugated to selected carriers yet still maintain sufficient characteristics of free cocaine to elicit anti-cocaine specific antibodies in vivo in a sufficiently high titer to mount a therapeutically effective immune response in vivo, that is, neutralizing a sufficient amount of free cocaine so that the pharmacological effects of cocaine are not experienced.

It is yet another object of the invention to provide drug/hapten carrier conjugates in a therapeutic composition suitable for combination with other therapeutics used in the treatment of drug addiction, particularly cocaine addiction.

It is another object of this invention to provide effective and alternative methods and routes of administration of the optimal therapeutic compositions, for example, stimulating a mucosal anti-cocaine IgA response in the lung and nasal passages, systemic IgG response and other antibody isotype responses.

It is yet another object of this invention to provide a therapeutic composition for acute toxicity following drug use by administering intact anti-drug mAb and especially Fab antibody fragments.

It is yet another object of this invention to provide a ELISA-based monitoring kit to determine the presence of cocaine antibody.

SUMMARY OF THE INVENTION

The present invention provides a therapeutic for drug addiction, particularly cocaine addiction, based on vaccination of subjects with a drug/hapten-carrier conjugate, and more particularly, a cocaine-protein conjugate. Therapeutic compositions of the invention comprise at least one hapten and at least one T cell epitope-containing carrier which when conjugated to form a hapten-carrier conjugate is capable of stimulating the production of anti-hapten antibodies. The hapten can be a drug or drug derivative, particularly cocaine. When the therapeutic composition containing the drug/ hapten carrier conjugate is administered to an addicted individual, anti-drug antibodies specific to the drug are elicited. A therapeutic immunization regimen elicits and maintains sufficiently high titers of anti-drug antibodies, that upon each subsequent exposure to the drug during the period of protection provided by the therapeutic, a sufficiently rapid and strong response neutralizes a sufficient amount of the drug such that the pharmacological effect of the drug is diminished, if not eliminated. Novel methods of preparing the conjugates are also disclosed.

These and other features, aspects and advantages of the present invention will become more apparent and better understood with regard to the following drawings, description and appended claims.

BRIEF DESCRIPTION OF THE DRAWINGS

FIG. 4 is a representation of "branches" at the sites of variability off the tropane ring in FIG. 1B of 4 molecules useful in preparing the conjugates of the instant invention.

FIG. 9A mice were immunized with PS-5.1/.6+CFA I.p

FIG. 10A shows that antiserum binding to a cocaine-protein conjugate can be competed off using free cocaine.

FIG. 10B is a bar graph showing that immune antiserum can bind [$^3$H]cocaine.

FIG. 12A shows the relative molecular weights of native (monomer and pentamer) and recombinant CTB (monomer).

FIG. 13A is a graph representing an ELISA where the anti-CTB antibody detects the ability of CTB to bind to ganglioside $G_{M1}$ on the ELISA plate.

FIG. 13B depicts a flow cytometry binding assay in which CTB is bound to eukaryotic cells expressing ganglioside $G_{M1}$.

FIG. 14A is a graph representing an ELISA in which native CTB and cocaine-CTB conjugate CTB-5.8 (PS-5.8 conjugated to CTB) are shown to be pentameric, based on their ability to bind to ganglioside $G_{M1}$.

FIG. 14B is a graph representing an ELISA in which CTB-5.8 (PS-5.8 conjugated to CTB) is bound to ganglioside $G_{M1}$ and the conjugate is detected with an anti-cocaine (anti-benzoylecognine) monoclonal antibody.

DETAILED DESCRIPTION OF THE INVENTION

Figure 1A:
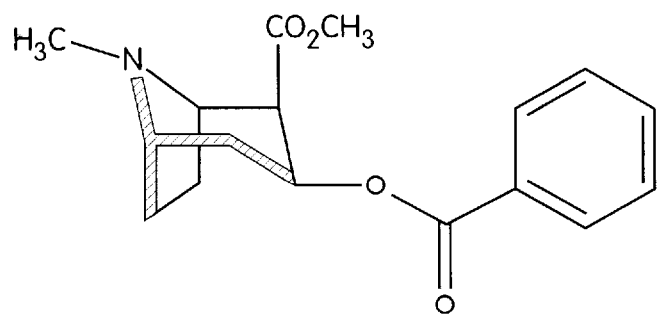
FIG. 1A is a representation of the structural formula of cocaine.

The patent and scientific literature referred to herein establishes the knowledge that is available to those skilled in the art. The issued U.S. Patents, PCT publications, and other publications cited herein are hereby incorporated by reference.

The present invention provides a therapeutic for drug addiction, particularly cocaine addiction, based on vaccination of an addicted individual with a drug-hapten-carrier conjugate, and more particularly, a cocaine-protein conjugate. Therapeutic compositions of the invention comprise at least one hapten and at least one T cell epitope containing carrier which when conjugated to form a hapten-carrier conjugate is capable of stimulating the production of anti-hapten antibodies. The hapten can be a drug or drug derivative. When the therapeutic composition containing the hapten/drug (or derivative thereof) is administered to the addicted individual, anti-drug antibodies specific to the drug are elicited. A therapeutic immunization regimen elicits and maintains sufficiently high titers of anti-drug antibodies, that upon subsequent exposure to the drug, neutralizing antibodies attach to a sufficient amount of the drug such that the pharmacological effects of the drug are diminished, if not eliminated. When the therapeutic composition is a cocaine-carrier conjugate, treatment induces an anti-cocaine antibody response which is capable of neutralizing cocaine in the bloodstream or mucosal tissue of a subject, thereby blocking the psychologically addictive properties of the drug. Since in the present invention cocaine will be neutralized before it can reach the central nervous system, the addict will receive no gratification from the use of cocaine. No side effects are expected from the administration of the therapeutic of the instant invention. For example, the drug is small and nonvalent and will not be able to cross-link antibody. Therefore, formation of immune complexes and the associated pathologies are not expected to occur. It is now, and is expected to be, compatible with current and future pharmacological therapies. Further, effective neutralization is long lasting. For example, neutralizing antibody responses against pathogens are known to last for years. Accordingly, it is expected that high-titer anti-drug antibodies elicited using the therapeutic composition of the instant invention can be maintained for long periods of time and possibly, at least a year. This long-term effect of the therapeutic composition with reduced compliance issues reduces recidivism which is a problem with current therapies.

Additionally, the therapeutic vaccination approach of the present invention to cocaine addiction is compatible with other therapies currently in use or in clinical trials. In fact, early phase co-therapy is highly desirable because of the time necessary to achieve optimal antibody titers. A number of diverse pharmacological agents would be suitable as co-therapies in preventing cocaine relapse, for example, desipramine, buprenorphine, naloxone, halperidol, chlorproazine, bromocriptine, ibogaine, as well as others that may become relevant.

The following are terms used herein, the definitions of which are provided for guidance. As used herein a hapten is a low-molecular-weight organic compound that reacts specifically with an antibody and which is incapable of inciting an immune response by itself but is immunogenic when complexed to a carrier forming a hapten-carrier conjugate. Further, the hapten is characterized as the specificity-determining portion of said hapten-carrier conjugate, that is, being capable of reacting with an antibody specific to the hapten in its free state. In a non-immunized addicted subject, there is an absence of formation of antibodies to the hapten. The therapeutic composition is used to vaccinate individuals who seek treatment for addiction to drugs. In the instant invention, the term hapten shall include the concept of a more specific drug/hapten which is a drug, an analog of a portion of the drug, or drug derivative. The therapeutic composition, or therapeutic anti-drug vaccine, when initially administered will give rise to a "desired measurable outcome". Initially, the desired measurable outcome is the production of a high titer of anti-drug antibodies (approximately at least 1 mg/ml of specific antibody in the serum). However, manipulation of the dosage regimen suitable for the individual gives and maintains a sustained "desired therapeutic effect." The desired therapeutic effect is the neutralization of free drug within a therapeutically acceptable time frame by anti-drug antibodies specific for the drug upon a subsequent exposure to the drug. Determining the therapeutically acceptable time frame is achieved by those skilled in the art by assessing the characteristics of the subject to be immunized, as well as the mode of administration. For example, cholera toxin is protective against live cholera for months. Using this and other vaccination protocols as a model, one skilled in that art would expect the immunity or the period of protection to last several months, up to about one year.

Passive immunization is also disclosed which means administration of or exposure to intact anti-drug mAb and especially Fab antibody fragments prepared using the novel conjugates of the instant invention. As stated above, passive immunization of humans with an anti-cocaine antibody of the present invention as a stand-alone treatment is less useful than active immunization. However, passive immunization would be particularly useful as an initial co-treatment and/or a supplementary complementary treatment (for example, during the period of time after initial administration of the vaccine but before the body's own production of antibodies) or in acute situations to prevent death (for example, when a person presents with a drug overdose).

The therapeutic composition of the instant invention, and more specifically, the therapeutic anti-drug vaccine, is a composition containing at least one drug/hapten-carrier conjugate capable of eliciting the production of a sufficiently high titer of antibodies specific to the drug/hapten such that upon subsequent challenge with the drug of the drug/hapten said antibodies are capable of neutralizing said drug. The expected immune response to a hapten-carrier conjugate is the formation of both anti-hapten and anti-carrier antibodies. The therapeutic level is reached when a sufficient amount of the anti-drug specific antibodies are elicited and maintained to mount a neutralizing attack on drug introduced after vaccination. The therapeutic regimens of the instant invention would allow for sufficient time for production of antibodies after initial vaccination and any boosting. Further, the optimal anti-drug vaccine contains at least one drug/hapten carrier conjugate comprising an optimal combination of the drug as hapten and a carrier so that production of anti-drug antibodies is capable of achieving an optimal therapeutic level, that is, remaining in vivo at a sufficiently high titer to withstand a subsequent challenge within several months with the selected drug. More particularly, the antibody titers remain sufficiently high to provide an effective response for about two months to about one year or more depending upon the individual, more usually at least three months. This optimal composition consists of a hapten-carrier conjugate, excipients and, optionally adjuvants.

When used in the treatment of cocaine, the present invention defines a hapten-carrier conjugate, wherein the hapten is cocaine or a cocaine derivative, which can be used to immunize mammals, particularly humans, to elicit anti-cocaine antibodies capable of binding free drug and preventing transit of the drug to the reward system in the brain thereby abrogating addictive drug-taking behavior. It is believed that cocaine affects the neuronal uptake of dopamine, norepinephrine, and serotonin on autoinhibitory receptors to inhibit the spontaneous firing of neurons. While not intending to exclude other modes of action, it is believed that once cocaine enters the blood stream following inhalation (snorting or smoking) or intravenous administration, it rapidly crosses the blood-brain barrier where the intact cocaine binds to specific recognition sites located on the dopamine transporter of mesolimbocortical neurons thereby inhibiting dopamine reuptake into presynaptic neurons. The euphoric rush is due to rapid build-up of dopamine in the synapse. The rapid action of cocaine presents problems unique to cocaine therapy. For this reason, cocaine remains the most complex and challenging, and before the present invention, elusive drug for which therapy is sought. Although estimates vary, it is believed that following intranasal administration, changes in mood and feeling states are perceived within about 2 to 5 minutes, and peak effects occur at 10 to 20 minutes. Thus, the active ingredient, the hapten-carrier conjugate, must be capable of eliciting fast acting antibodies. The duration of cocaine effects rarely exceed 1 hour following intranasal administration. Thus, it is desirable that the duration of the response be at least that long. Cocaine free-base, including the free-base prepared with sodium bicarbonate (crack), has a relatively high potency and rapid onset of action, approximately 8 to 10 seconds following smoking. An embodiment of the instant invention is capable of an exceedingly rapid and specific response capable of neutralizing cocaine within this time frame. Due to the route of the circulation, i.v. cocaine is intermediate in time of onset of euphoria taking from about 30 seconds to about 1 minute. Thus, when used in the treatment of cocaine abuse, the therapeutic composition of the instant invention, anti-cocaine antibodies alter the physiological response to cocaine in humans. These antibodies possess the appropriate bioavailability and speed of binding that is required to neutralize cocaine in vivo The Examples herein describe experiments done in mice to simulate alteration of response in mammals.

At the outset, the therapeutic protocol will be aimed at a single drug. Initial vaccination with the therapeutic composition of the present invention will create high titers of hapten-specific antibodies in vivo. Typically, this process takes up to about three weeks to elicit high titer antibodies. Periodic tests of the vaccinated subjects plasma are useful to determine individual effective doses. Titer levels are increased and maintained through periodic boosting. It is anticipated that this therapeutic will be used in combination with current drug rehabilitation programs, including counseling. Further, the therapeutic composition of the present invention are aimed at several drugs simultaneously or in succession and may be used in combination with other therapies. For example, the therapeutic compositions and methods of the instant invention are used without adverse interactions in combination with conventional pharmacological approaches and previously discussed "short term" passive immunization and possible active immunization against transition states to enhance the overall effect of therapy.

The therapeutic composition of the present invention is prepared by coupling one or more hapten molecules to a protein carrier to obtain a hapten-carrier conjugate capable of stimulating T cells (immunogenic) which leads to T cell proliferation and a characteristic release of mediators which activate relevant B cells and stimulate specific antibody production. Antibodies of interest are those specific to the hapten portion of the hapten-carrier conjugate (also called the hapten-carrier complex).

Therapeutic compositions containing a combination of conjugates, either to the same drug (cross-immunization) or to multiple drugs (co-immunization) are disclosed. Such co-mixtures of conjugates of multiple drugs are particularly useful in the treatment of polydrug abuse.

Figure 6:
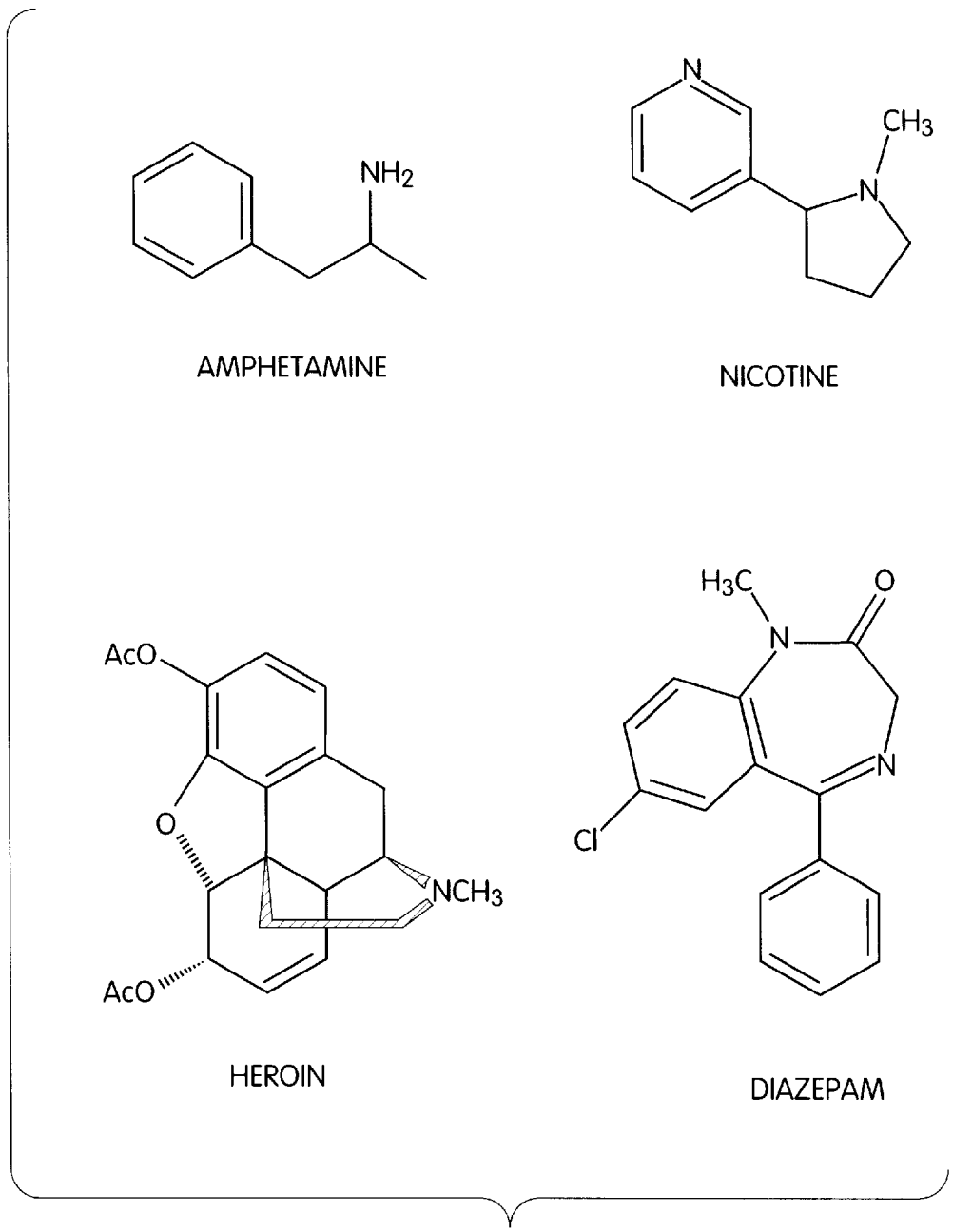
FIG. 6 is a representation of the structures of four alternative drugs of abuse suitable for conjugation and administration in accordance with the teachings of the instant invention.

In selecting drug suitable for conjugation according to the instant invention, one skilled in the art would select drug with properties likely to elicit high antibody titers. That is, antibodies raised against a molecule that is similar to molecules which are endogenous to the individual could cross-react with many different molecules in the body giving an undesired effect. That is, the drug to be selected as the hapten (drug/hapten) must be sufficiently foreign and of a sufficient size so as to avoid eliciting antibodies to molecules commonly found inside a human body. For example, for these reasons, alcohol would not be suitable for the therapeutic of the instant invention. Moreover, the antibodies raised against the therapeutic composition are highly specific and of a sufficient quantity to neutralize the drug either in the blood stream or in the mucosa or both. Without limiting the invention, the drugs which are suitable for therapeutic composition (not in order of importance) are:

Hallucinogens, for example mescaline and LDS;

Cannabinoids, for example THC;

Stimulants, for example amphetamines, cocaine, phenmetrazine, methylphenidate;

Nicotine;

Depressants, for example, nonbarbiturates (e.g. bromides, chloral hydrate etc.), methaqualone, barbiturates, diazepam, flurazepam, phencyclidine, and fluoxetine;

Opium and its derivatives, for example, heroin, methadone, morphine, meperidine, codeine, pentazocine, and propoxyphene. FIG. 6 shows the structure of four drugs suitable for conjugation according to the instant invention.

Carrier proteins have been used in conjugate vaccines. Three vaccines for *Haemophilus influenza* type b that utilize different carrier proteins currently are on the market. In these vaccines, selected carrier proteins are conjugated to various oligosaccharides. ProHIBiT$_{13}$ (Connaught Laboratories, Inc.) uses diphtheria toxin as a carrier protein, HibTITER__ (Lederle) uses a non-toxic variant of diphtheria toxin and PedvaxHIB__(Merck & Co.) uses the outer membrane complex of *Neisseria meningitidis* as a carrier for the oligosaccharides. Each conjugate vaccine has its own issues surrounding the production and formulation of effective conjugate vaccines.

The carrier of the instant invention is a molecule containing at least one T cell epitope-containing molecule which is capable of stimulating the T cells which in turn help the B cells initiate and maintain sustained antibody production to portions of the entire conjugate, including the hapten portion. Thus, since a carrier is selected because it is immunogenic, a strong immune response to the vaccine in a diverse patient population is expected. The carrier, like the hapten, must be sufficiently foreign to elicit a strong immune response to the vaccine and to avoid the phenomenon of carrier-induced epitope suppression. A conservative, but not essential, approach is to use a carrier to which most patients have not been exposed. However, even if carrier-induced epitope suppression does occur, it is manageable as it has been overcome by dose (DiJohn et al., *Lancet*, 1415–1418, 1989) and other protocol changes (Etlinger et al., *Science*, 249:423–425(1990)), including the use of CTB (Stok et al., *Vaccine*, 12:521–526 (1994)). Still further, carriers containing a large number of lysines are particularly suitable for conjugation according to the methods of the instant invention. Suitable carrier molecules are numerous and include, but are not limited to, Bacterial toxins or products, for example, cholera toxin B (CTB), diphtheria toxin, tetanus toxoid, and pertussis toxin;

Lectins, for example, ricin-B subunit, abrina and sweet pea;

Sub virals, for example, retrovirus nucleoprotein (retro NP), rabies ribonucleoprotein (rabies RNP), plant viruses (e.g. TMV), vesicular stomatitis virus-nucleocapsid protein (VSV-N), recombinant small pox subunit;

Artificial vehicles, for example, multiantigenic peptides (MAP), microspheres; and others such as malarial antigens, proteins, peptides as well as any modifications, derivatives or analogs of the above.

In yet another embodiment, various proteins or peptides fragments, analogs, of allergens are used are carriers. These carriers are chosen because they are immunogenic and will have a T cell response capable of providing help for a anti-hapten antibodies Examples of and methods of making allergen proteins and peptides and their sequences are disclosed in U.S. Ser. No. 08/350,225 filed Dec. 4, 1994 the teachings of which are incorporated herein by reference. Using the methods and compositions of the present invention, and more particularly, the techniques set out in the Examples below, one skilled in the art links the selected drug/hapten with the selected carrier to make the hapten-carrier conjugate of the instant invention. A particularly suitable allergen is *Cryptomeria japonica*, more particularly, recombinant Cryj 1 the sequence of which has been published with slight variation (IA, pCryj 1 FL, ISP and IB). First, in countries other than Japan, *Cryptomeria japonica* is not prevalent, therefore previous exposure to the Cry j 1 allergen will fit one of the criteria of a suitable carrier, that is, sufficiently foreign. Further, Cry j 1 elicits excellent antibody response but will not cross-react with the native allergen eliminating the possibility of adverse reaction.

To determine features of suitable carriers, initial experiments were performed using bovine serum albumin as a protein carrier. The protein has been ideal for animal experiments, as it is inexpensive and contains large numbers of lysines for conjugation. However, it is less appropriate for human vaccination because the generation of anti-BSA antibodies has the potential to cause adverse responses. Thus, using the results of these experiments, applicants applied the criteria to a large number of candidate carriers and found those listed above suitable for the practice of the instant invention. For reasons discussed in more detail herein, CTB is selected as a particularly attractive candidate as a carrier, particularly for a human vaccine against cocaine. First, it is a highly immunogenic protein and is capable of stimulating strong systemic and mucosal antibody responses(Lycke, N.Y., *J. Immunol*, 150:4810–4821 (1992)). Second, CTB has the potential to generate a strong mucosal antibody response against the cocaine hapten (Holmgren et al., *Am. J. Trop. Med. Hyg.*, 50:42–54 (1994)), (Silbart et al., *J. of Immun. Methods*, 109:103–112 (1988)), (Katz et al., *Infection and Immun.*, 61:1964–1971 (1993)). This combined IgA and IgG anti-hapten response is highly desirable in blocking cocaine that is administered nasally or by inhalation. Third, it is already being shown to be safe for human use in clinical trials for cholera and enterotoxigenic *E. coli* vaccines (Holgren et al, supra), (Jertborn et al., *Vaccine*, 12:1078–1082 (1994)), (The Jordan Report, Accelerated development of vaccines 1993., NIAID, 1993). Fourth, most cocaine addicts in the U.S. have not been exposed to cholera and therefore will not already be immune to CTB.

The carrier of a preferred embodiment is a protein or a branched (i.e, MAP) or single chain peptide. A suitable carrier is a protein or fragment thereof which is not commonly used in vaccination in the country in which the therapy is used, thereby avoiding the potential of "carrier induced epitopic suppression." For example, in the United States where standard childhood immunization includes diphtheria and tetanus, proteins such as tetanus toxoid and diphtheria toxoid, if unmodified, may be less desirable as appropriate carriers. Further, the carrier protein should not be a protein to which one is tolerant. For example, in humans, this would exclude unmodified human serum albumin. Further, many food proteins would have to be carefully screened before use as a carrier. Again, for example, in humans, bovine serum albumin would be less desirable due to the beef in the diet of most humans. Still further, it is highly advantageous if the carrier has inherent immunogenicity/adjuvanticity. A delicate balance must be struck between the desire for immunogenicity of the carrier and the desire to maximize the anti-hapten antibody. Still further, the preferred carrier would be capable of both systemic response and response at the site of exposure. This is particularly true of cocaine which is more frequently administered across mucosal membranes. The speed of response is especially critical where cocaine has been smoked. Accordingly, in the case of cocaine, a suitable carrier elicits not only a systemic response but also a pre-existing mucosal antibody response. In such a mucosal response the reaction of antibodies with cocaine would happen rapidly enough to counteract the drug before it begins circulating in the blood stream. In one embodiment of the present invention, the therapeutic composition acts within the approximately 8 to 10 seconds it takes for the cocaine to travel from the lungs through the heart to the brain. This ability is achieved through the careful selection of the carrier molecule. One such ideal carrier is cholera toxin B (CTB) as well as other with the ability to enhance a mucosal response, more particularly, LTB family of bacterial toxins, retrovirus nucleoprotein (retro NP), rabies ribonucleoprotein (rabies RNP), vesicular stomatitis virus-nucleocapsid protein (VSV-N), recombinant small pox subunit; and multiantigenic peptides (MAP).

Production of recombinant B subunit of cholera toxin

Cholera toxin is the enterotoxin produced by *Vibrio cholerae* and consists of five identical B subunits with each subunit having a molecular weight of 11.6 KDa (103 amino acids) and one A subunit of 27.2 KDa (230 amino acids) (Finkelstein R. A., *Immunochem& Molecular Genetic Analysis of Bac. Path.*, 85–102 (1988)). The binding subunit, CTB, binds to ganglioside $G_{M1}$ on the cell surface (Sixma et al., *Nature*, 351:371–375 (1991)), (Orlandi et al., *J. Biol. Chem.*, 268:17038–17044 (1993)). CTA is the enzymatic subunit which enters the cell and catalyzes ADP-ribosylation of a G protein, constitutively activating adenylate cyclase (Finkelstein R. A., Immunochem & Molecular Genetic Analysis of Bac. Path., 85–102 (1988)). In the absence of the A subunit, cholera toxin is not toxic.

Figure 12A:
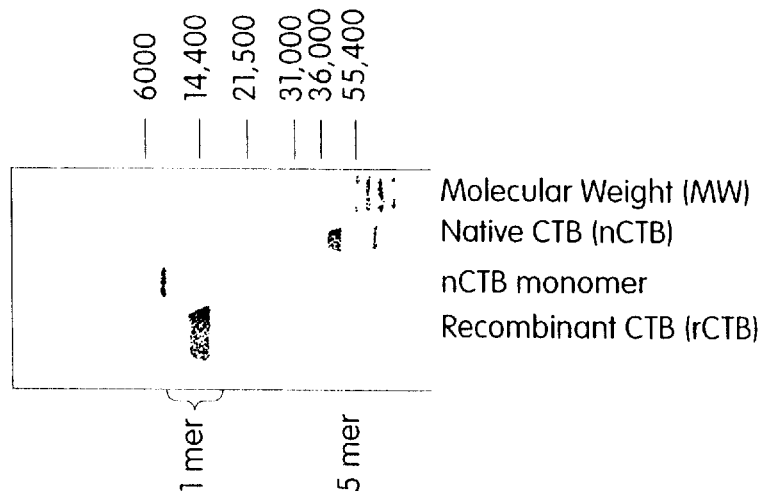
FIGS. 12A, B, and C show some of the properties of the cholera toxin-B subunit, a carrier used in some conjugates prepared according to the teachings of the instant invention.

Others have disclosed the production of high level recombinant expression of CTB pentamers (L'hoir et al., *Gene*, 89:47–52 (1990), Slos et al., *Protein Exp. and Purif.*, 5:518–526 (1994)). While native CTB is commercially available, it is frequently contaminated with (approximately 0.1 %) CTA. Therefore, applicants have expressed recombinant CTB in *E. coli* and developed assays for its characterization. The choleragenoid construct was purchased from the American Type Culture Collection (pursuant to U.S. Pat. No. 4,666,837). Recombinant CTB was cloned from the original vector (pRIT10810) into an expression plasmid (pET11d, Novagen) with an extra N-terminal sequence containing a $His_6$ tag and expressed in *E. coli* to the level of 25 mg/liter of culture. The protein was purified over a $Ni^+$column using standard techniques and analyzed on SDS-PAGE (see FIG. 12a, b and c). The recombinant CTB is monomeric in this assay and is larger than the native CTB monomer due to the N-terminal extension.

Figure 12B:
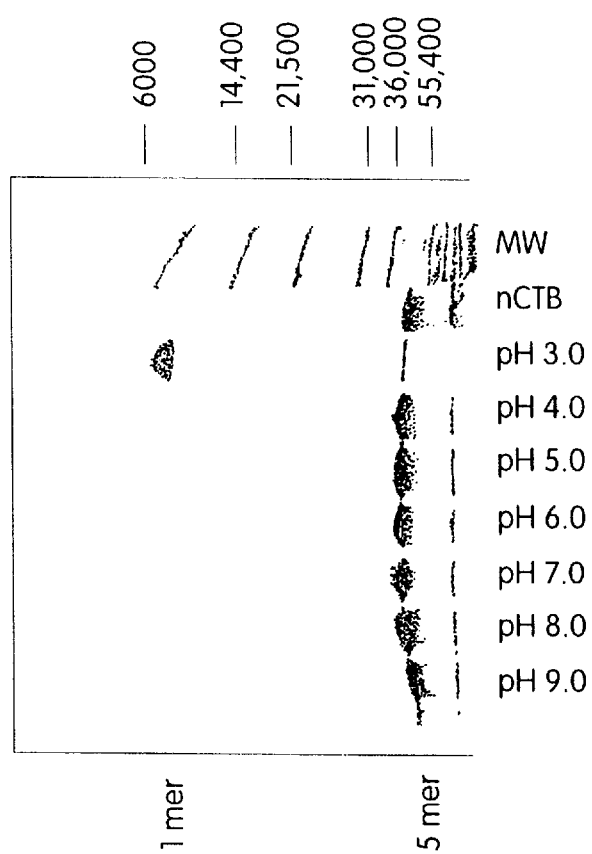
FIG. 12B illustrates the stability of the CTB pentamers over a pH range of 3–9.
Figure 13A:
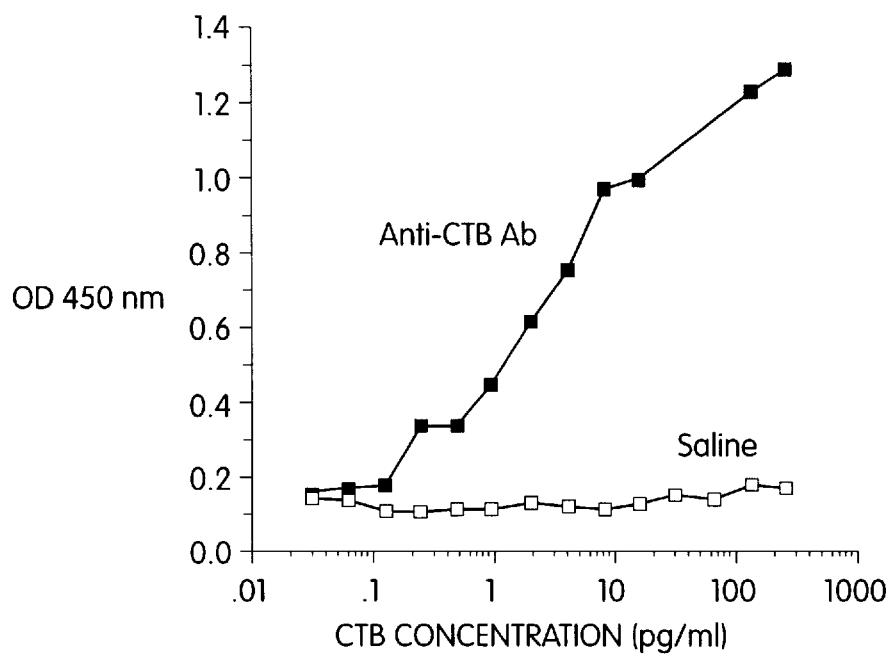
FIG. 13A and 13B demonstrate assay systems used to validate the functional activity of rCTB.
Figure 13B:
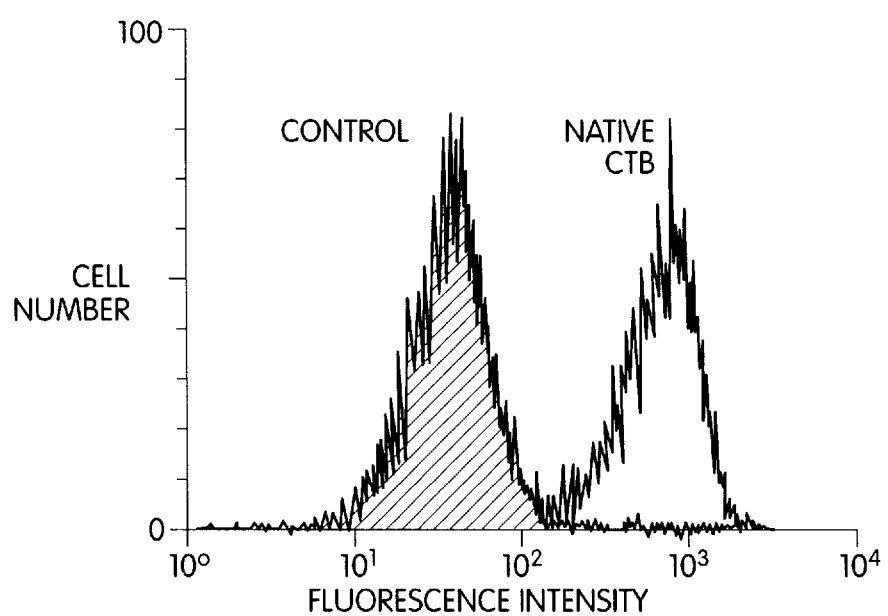

The pentameric structure of CTB is required for binding to ganglioside $G_{M1}$. The pentamer is stable to SDS as long as the samples are not boiled, permitting pentamerization to be assessed by SDS-PAGE. The gel in FIG. 12A demonstrates that the native CTB is a pentamer and is readily distinguishable from the denatured monomeric CTB. Pentamer structure is maintained over a pH range from 4 to 9 (see FIG. 12B), which facilitates a variety of conjugation chemistries. The recombinant CTB initially expressed is monomeric and one way to obtain pentameric CTB is by making adjustments to express properly folded pentameric CTB. It has been found that cytoplasmic expression provides a much higher levels of monomeric CTB. One skilled in the art would be aware of methods of folding monomeric CTB into pentameric CTB. An alternative to re-folding monomeric CTB to obtain pentameric CTB is periplasmic expression which resulted in pentameric recombinant CTB able to bind $G_{M1}$-ganglioside by ELISA, FIG. 13A and FIG. 13B show the data supporting this finding. One skilled in the art may find several approaches for obtaining pentameric recombinant CTB have been described, including periplasmic expression with a leader (Slos et al., supra), 58(Sandez et a., *Proc. Nat'l. Acad. Sci.*, 86:481–485 (1989), (Lebens et a., *BioTechnol.*, 11:1574–1578 (1993)) or post-translational refolding L'hoir et al, supra), (Jobling et al., *Molecular Micorbiol.*, 5:1755–1767 (1991)).

Still another alternative for improved mucosal response is the use of CTA. That is, although CTB retains the adjuvant activity of the holotoxin in most instances, it has been reported the enzymatically active A subunit enhances activity (Liang et a., *J. Immunol.* 141:1495–1501 (1988)), Wilson et al., *Vaccine*, 11:113–118 (1993)) and (Snider et al., *J. Immunol.* 153:647 (1994)). However, purified native or recombinant CTB is preferred.

A difficult aspect of achieving the conjugate of the instant invention involves modifying the hapten, and more particularly the cocaine or cocaine derivative, sufficiently to render it capable of being conjugated or joined to a carrier while maintaining enough of the structure so that it is recognized as free state hapten, or more particularly free cocaine. It is essential that a vaccinated individual has antibodies which recognize free cocaine. This is demonstrated by the LD50 experiments which are explained in more detail in the Examples. Antibodies of interest are hapten-specific antibodies and, more particularly, cocaine-specific antibodies. Further, the term antibody (whether used in the singular or plural) when referring to cocaine-specific antibodies elicited as a result of the therapeutic compositions and methods of the instant invention contemplate that more than one cocaine-specific antibody may be elicited. It should be recognized, however, that principles and methods used to describe the preferred embodiments may be extended from this disclosure to a wide range of hapten-carrier conjugates useful in the treatment of a variety of drug addictions and toxic responses.

Conjugates

Figure 2B:
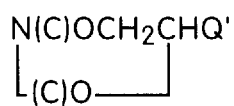
FIGS. 2A and B are representations of a number of possible arbitrarily labeled "branches" identified for ease of understanding suitable compounds and conjugates used in the practice of the instant invention.
Figure 2B:
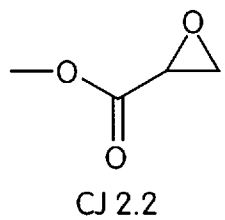
Figure 2B:
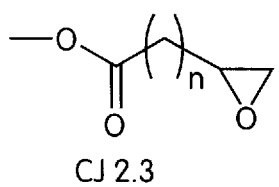
Figure 2B:
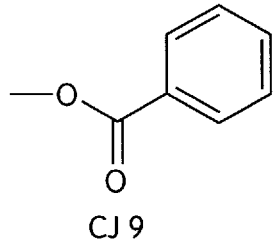
Figure 2B:
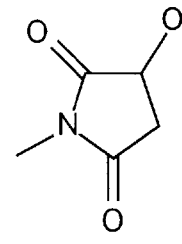

Preparation of the novel cocaine-carrier conjugates of the instant invention are derived from cocaine and cocaine metabolites, primarily derivatives of norcocaine, benzoyl ecgonine and ecgonine methyl ester. FIG. 4 shows a representation of the cocaine molecule as compared to these molecules. In the case of norcocaine and ecgonine methyl ester, the secondary amine and the secondary alcohol functional groups present in the two compounds respectively, are modified to provide a chemical linkage which enables attachment to a protein carrier. In the case of benzoyl ecgonine, the free acid is either used directly to attach to a carrier protein or is modified with a linkage to facilitate the same. The length and nature of the linkage is such that the hapten is displaced a sufficient distance from the carrier protein domain to allow its optimal recognition by the antibodies initially raised against it. The length of the linker is optimized by varying the number of - $CH_2$ - groups which are strategically placed within a "branch" selected from the group consisting of:

CJ 0 Q
CJ 1 $(CH_2)_nQ$
CJ 1.1 $CO_2Q$
CJ 1.2 COQ
CJ 2 $OCO(CH_2)_nQ$
CJ 2.1 OCOCH=Q
CJ 2.2 $OCOCH(O)CH_2$
CJ 2.3 $OCO(CH_2)_nCH(O)CH_2$
CJ 3 $CO(CH_2)_nCOQ$
CJ 3.1 $CO(CH_2)_nCNQ$
CJ 4 $OCO(CH_2)_nCOQ$
CJ 4.1 $OCO(CH_2)_nCNQ$
CJ 5 $CH_2OCO(CH_2)_nCOQ$
CJ 5.1 $CH_2OCO(CH_2)_nCNQ$
CJ 6 $CONH(CH_2)_nQ$
CJ 7 $Y(CH_2)_nQ$
CJ 7.1 $CH_2Y(CH_2)_nQ$
CJ 8 $OCOCH(OH)CH_2Q$
CJ 8.1 $OCO(CH_2)_nCH(OH)CH_2Q$
CJ 9 $OCOC_6H_5$
CJ 9.1 $OCOC_6H_4Q$ and
CJ 10 shown on FIG. 2b and shown in FIG. 2b herein. The $(CH_2)_n$ groups number from about 3 to about 20, more particularly about 3 to about 6. Y is selected from the group consisting of S, O, and NH. Q is selected from the group consisting of:

(1) —H
(2) —OH
(3) —$CH_2$
(4) —$CH_3$
(4a) —$OCH_3$
(5) —COOH
(6) halogen
(7) protein carrier
(8) modified protein carrier
(9) activated esters, such as 2-nitro-4-sulfophenyl ester and N-oxysuccinimidyl ester
(10) groups reactive towards carriers or modified carriers such as
    mixed anhydrides,
    acyl halides,
    acyl azides,
    alkyl halides,
    N-maleimides,
    imino esters,
    isocyanate,
    isothiocyanate; or
(11) another "branch" identified by its "CJ" reference number. A "modified carrier protein" is any carrier thiolated with 2-iminothiolane (Traut's reagent). For simplicity, $(CH_2)_nQ$, where Q=H, may be referred to as $(CH_3)$, methyl or Me, however, it is understood that it fits into the motif as identified in the "branches" as shown in FIG. 2a & b.

Further abbreviations used herein include:
BSA=Bovine serum albumin
DCC=Dicyclohexylcarbodiimide
DMF=N,N'-Dimethylformamide
EDC (or EDAC)=N-ethyl-N'-(3-(dimethylamino) propyl) carbodiimide hydrochloride
EDTA=Ethylenediamine tetraacetic acid, disodium salt
HATU=O-(7-Azabenzotriazol-1-yl)-1,1,3,3-tetramethyluronium hexafluorophosphate NMM=N-methylmorpholine Further the IUPAC nomenclature for several named compounds are:

Norcocaine
3β-(Benzoyloxy)-8-azabicyclo[3.2.1]octane-2β-carboxylic acid methyl ester Benzoyl ecgonine
3β-(Benzoyloxy)-8-methyl-8-azabicyclo[3.2.1]octane-2β-carboxylic acid Cocaine
3β-(Benzoyloxy)-8-methyl-8-azabicyclo[3.2.1]octane-2β-carboxylic acid methyl ester Ecognine methyl ester
3β-(Hydroxy)-8-methyl-8-azabicyclo[3.2.1]octane-2β-carboxylic acid methyl ester PS-2 compounds
3β-(Bromoacetyloxy)-8-methyl-8-azabicyclo[3.2.1]octane-2β-carboxylic acid methyl ester PS4
3β-(Succinoyloxy)-8-methyl-8-azabicyclo[3.2.1]octane-2β-carboxylic acid methyl ester PS-5 compounds
3β-(Benzoyloxy)-8-succinoyl-8-azabicyclo[3.2.1]octane-2β-carboxylic acid methyl ester
3β-(Benzoyloxy)-8-chlorosuccinoyl-8-azabicyclo[3.2.1]octane-2β-carboxylic acid methyl ester
3β-(Benzoyloxy)-8-(N-oxysuccinimidoyl)succinoyl-8-azabicyclo[3.2.1]octane-2β-carboxylic acid methyl ester
3β-(Benzoyloxy)-8-(2-nitro-4-sulfophenyl ester)succinoyl-8-azabicyclo[3.2.1]octane-2β-carboxylic acid methyl ester PS-6 compounds
3β-(Benzoyloxy)-2β-(hydroxymethyl)-8-methyl-8-azabicyclo[3.2.1]octane
3β-(Benzoyloxy)-2β-(hydroxymethyl succinoyl)-8-methyl-8-azabicyclo[3.2.1]octane Reactions In one embodiment, compounds of the instant invention are synthesized by acylating ecgonine methyl ester with bromoacetyl bromide in DMF in the presence of two equivalents of diisopropylethylamine. The product is then coupled to the thiol group of a thiolated carrier protein to obtain a conjugate with the general structure of PS-2 (see FIG. 3a and Example 1)

In another embodiment, compounds of the instant invention are synthesized by succinylating ecgonine methyl ester with succinic anhydride in DMF in the presence of one equivalent of triethylamine. The product is then coupled to the ε amino group of a lysine residue of a carrier protein to obtain a conjugate with the general structure of PS-4 (see FIG. 3a and Example 2).

In yet another embodiment, compounds of the instant invention are synthesized by reacting norcocaine with succinic anhydride in DMF in the presence of two equivalents of triethylamine. The product is then coupled to the ε amino group of a lysine residue of a carrier protein using EDC to obtain a conjugate with the general structure of PS-5 (see FIG. 3a and Method A of Example 3)

Conjugates with the general structure of PS-5 may be obtained in an alternative set of reactions. In this alternative, the protein conjugation can be carried out using a pre-activated succinylated norcocaine derivative. That is, the intermediate can be isolated and characterized. The pre-activated succinylated norcocaine derivative is synthesized by reacting 4-hydroxy-3-nitrobenzene sulfonic acid sodium salt with succinylated norcocaine in the presence of dicyclohexylcarbodiimide (DCC) and DMF. The product is conjugated to the ε amino group of a lysine residue of a carrier protein to obtain a conjugate with the general structure of PS-5 (See FIG. 3a and Example 3)

In still another embodiment, compounds of the instant invention are synthesized by reacting succinylated norcocaine with N-hydroxysuccimide in the presence of ethyl chloroformate, N-methylmorpholine (NMM) and DMF. The product is then coupled to the ε amino group of a lysine residue of a carrier protein to obtain a conjugate with the general structure of PS-5 (see FIG. 3a).

In another embodiment, compounds of the instant invention are synthesized by reacting thionyl chloride with succinylated norcocaine. The product is then conjugated to a carrier protein to obtain a conjugate with the general structure of PS-S (see FIG. 3a).

In yet another embodiment, compounds of the instant invention, are synthesized by reacting succinylated norcocaine with DMF, diisopropylethylamine and HATU in DMF (Carpino, Louis (1993) J. Am. Chem. 115, 4397–4398) The product was added to an aqueous solution containing the carrier protein to obtain a conjugate with the general structure of PS-5 (see FIG. 3a).

Alternatively, compounds of the instant invention are synthesized by succinylating the carrier protein with succinic anhydride in borate buffer. The product is then coupled to norcocaine in the presence of EDC to obtain a conjugate with the general structure of PS-5 (see FIG. 3a and Method B of Example 3).

In another embodiment, compounds of the instant invention are synthesized by reducing the free acid in benzoyl ecgonine to its corresponding primary alcohol, using borane-dimethylsulfide complex. The alcohol is reacted with succinic anhydride in DMF, the product of which is then conjugated to the free amino acid group of a carrier protein in the presence of EDC to obtain a conjugate with the general structure of PS-6 (see FIG. 3a).

Figure 3A:
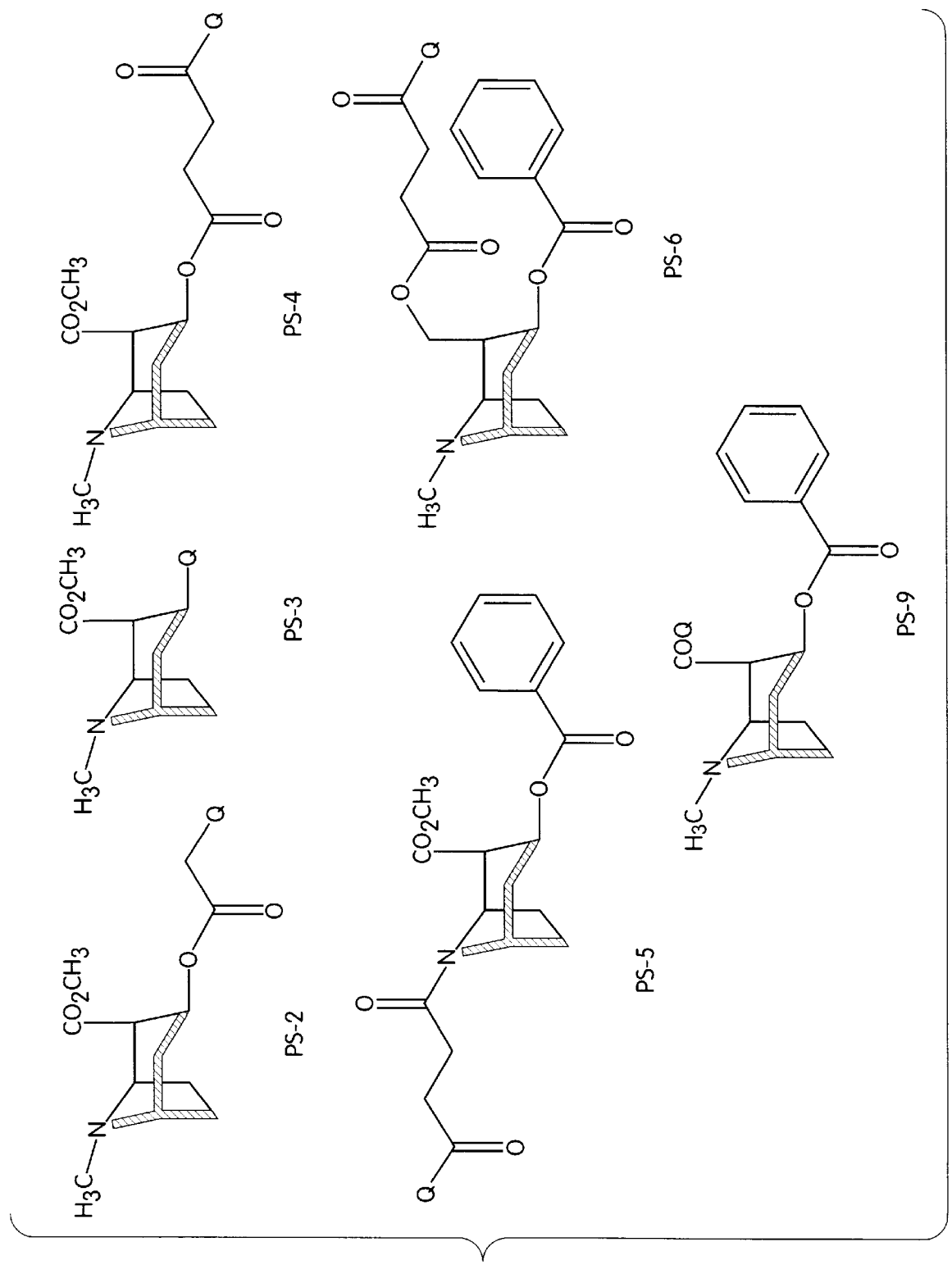
FIG. 3A is a representation of 6 cocaine conjugates (PS-2,3,4,5,6, and 9) of the instant invention FIGS. 3B(1) and (2) is a representation of "branches" at the sites of variability off the tropane ring of cocaine of the 6 cocaine conjugates (PS-2,3,4,5,6, and 9) as well as other conjugates and intermediates of the instant invention.
Figure 5:
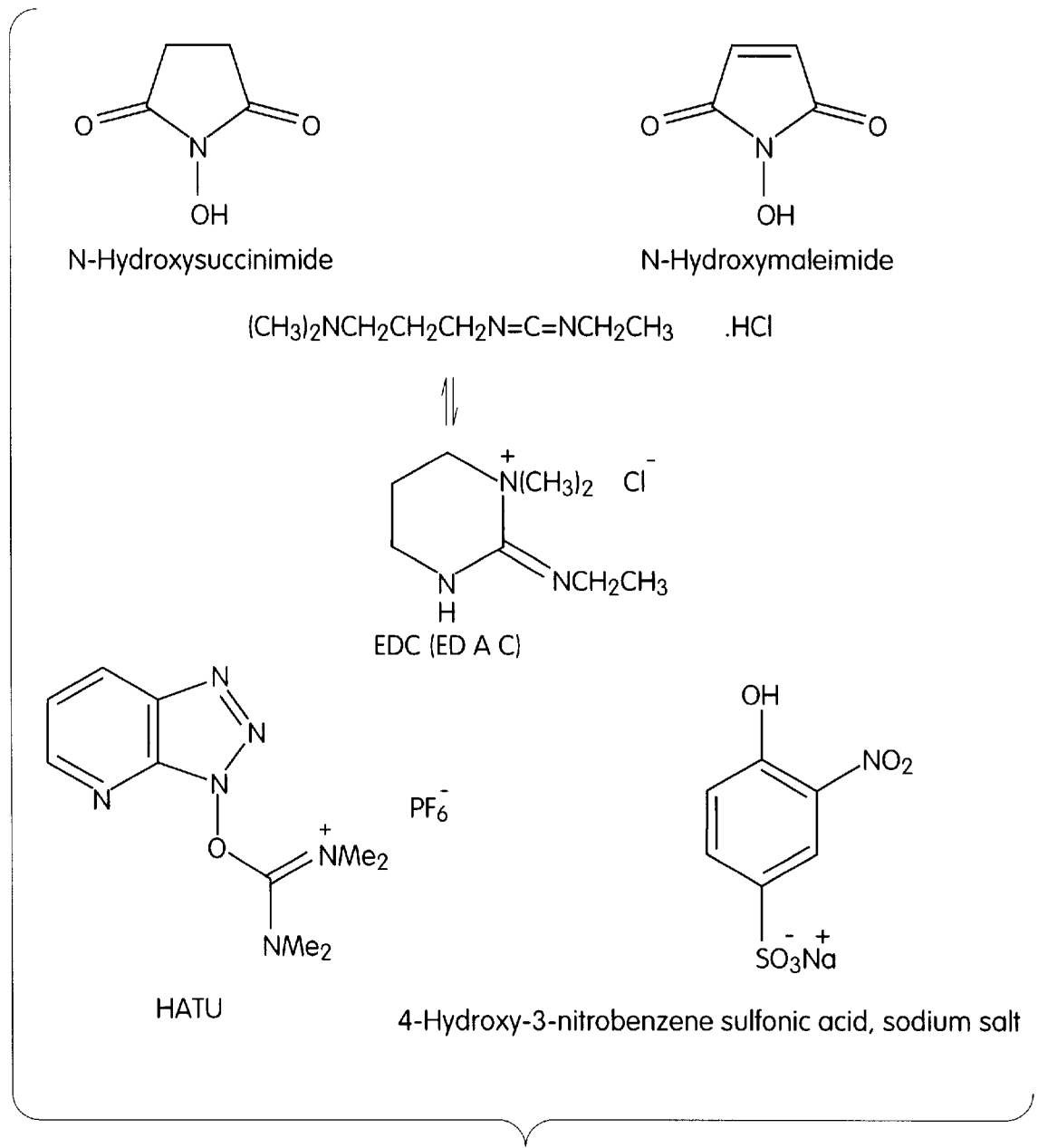
FIG. 5 is a representation of the structures of five reagents useful in the practice of the instant invention.

In another embodiment, compounds of the instant invention are synthesized by conjugating benzoyl ecgonine to the ε amino group of a lysine residue of a carrier protein in the presence of EDC to obtain a conjugate with the general structure of PS-9 (see FIG. 3a).

The PS-5 analogs of CTB are synthesized using the same protocols established using BSA as a protein carrier which are more specifically described in the Examples. The degree of haptenation is determined by time of flight (TOF) mass spectral analysis. Table 2 shows that haptenation was achieved using several conjugates (some with CTB as a carrier) made pursuant to the methods of the instant invention. Different batches are indicated by adding a decimal and a number thereafter, e.g., PS-5 batch 6 is PS-5.6.

TABLE 2

| Conjugate | Carrier | # Haptens |
| --- | --- | --- |
| PS-5.6 | CTB* | 1.25 |
| PS-5.7 | CTB* | <1 |
| PS-5.8 | CTB* | 1.9 |
| PS-5.9 | CTB* | 0.9–6.5 |
| PS-5.10 | CTB* | 2.3–6.8 |
| PS-5.11 | CTB* | 1.0–7.8 |
| PS-5.12 | CTB* | 1.6 |
| PS-5.13 | CTB* | 2.3–8.5 |
| PS-2.2 | BSA | 16 |
| PS-4.3 | BSA | 24 |

TABLE 2-continued

| Conjugate | Carrier | # Haptens |
|---|---|---|
| PS-5.1 | BSA | 4 to 20 |
| PS-5.4 | BSA | 29 |
| PS-5.5 | BSA | 22 |
| PS-5.6 | BSA | 27 |
| PS-5 | HEL | 1 to 3 |
| PS-6.1 | BSA | 9 |
| PS-6 | HEL | 2 |
| PS-9 | BSA | 1 or 2 |
| PS-9.2 | BSA | 7 |

With CTB as the carrier, the number of haptens refers to the "# Haptens" refers to the number of haptens per monomer.

Compounds PS-2, PS-3, PS4, PS-5, PS-6 and PS-9 are novel conjugates. Other conjugates are listed in FIG. 3b(1) and (2). Following the novel methods disclosed, one skilled in the art could synthesize compounds PS-10 to PS-26 (see FIG. 3b(1) AND (2)).

Figure 1B:
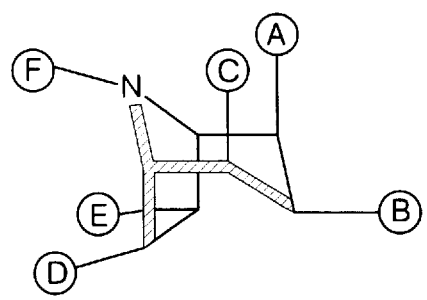
FIG. 1B is a diagram representing sites of variability when preparing a cocaine conjugate of the instant invention. The sites of variability are arbitrarily assigned to easily designate the compound and conjugates of the instant invention and not necessarily reaction sites.
Figure 15:
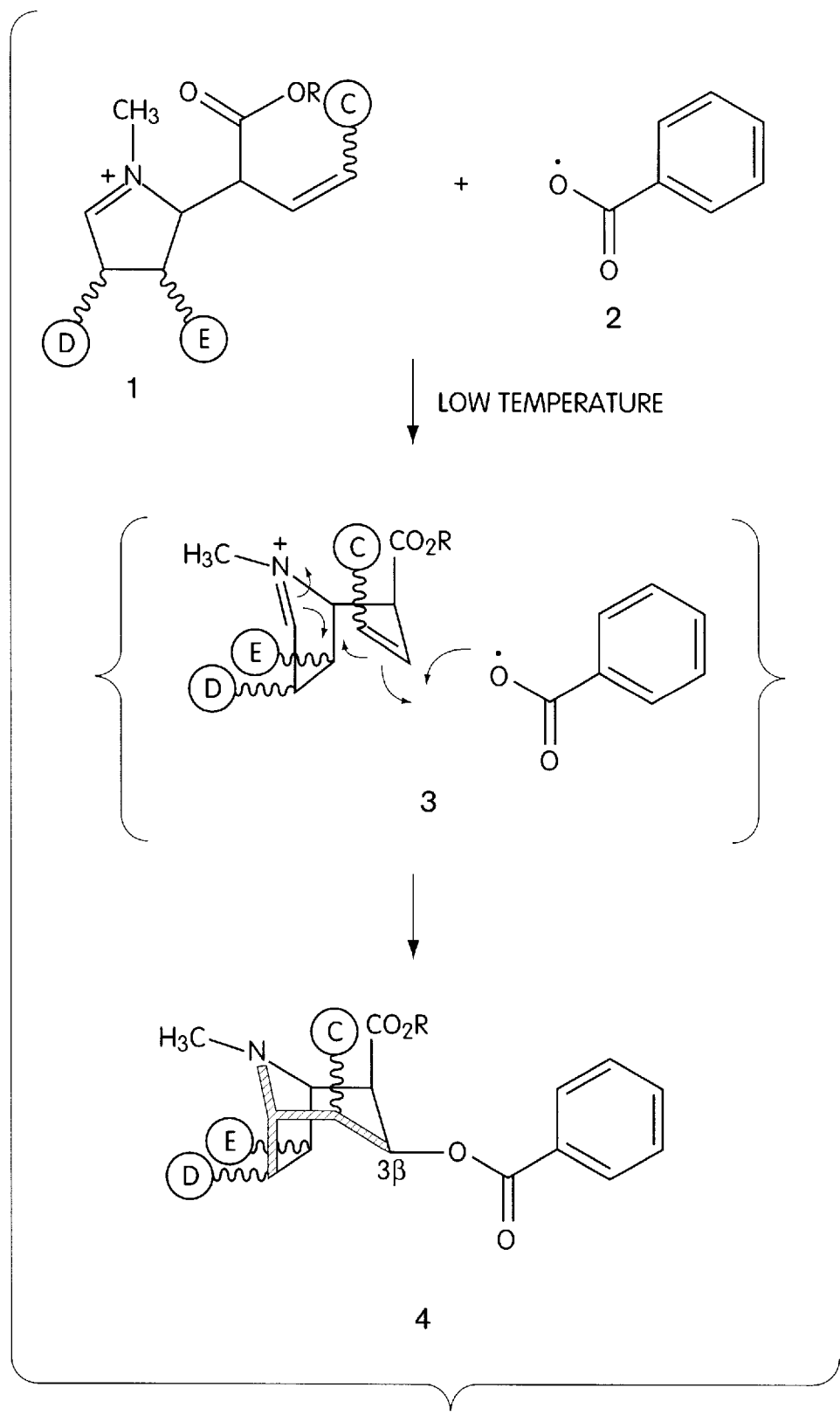
FIG. 15 is a schematic of another reaction useful in the preparation of conjugates of the instant invention, in particular, 3 β benzoate ester adduct 4.

In yet another embodiment, compounds PS-27 to PS-50 are synthesized via a series of reaction which allow a novel entry into the tropane class of alkaloids. This novel route involves a free radical mediated 1,6 diene-like intermolecular cyclization (March., J., Advanced Organic Chemistry: Reactions, Mechanisms and Structure, (19**) 4th ed., Wiley-lnterscience, 744 and references cited therein). Tropane alkaloids, in particular cocaine and its analogs, have been previously synthesized, however these routes involve multiple steps and usually resolution of an intermediate (Wilstatter et al. (1923) "Synthesis of Natural Cocaine", Ann. Chem. 434, 111–139; Tufariello, et al (1979) "Synthesis in the Tropane Class of Alkaloids", J. Am. Chem. 101, 2435–2442); Lewin et al. (1987) J. heterocyclic Chem., 24, 19–21 and Simoni et al, (1993) J. Med Chem 36, 3975–3977). Although limited to the synthesis of 3-aryltropane derivatives, Davies et al (U.S. Pat. No. 5,262,428), synthesized cocaine analogs by decomposing vinyldiazothanes in the presence of pyrroles to form a tropane ring which is then followed by a Grignard addition to provide the cocaine analogs. In this alternative embodiment, novel cocaine-carrier conjugates with "remote site" branches are synthesized. As used herein "remote sites" are labeled C. D and E on FIG. 1. Those sites pose special challenges to the chemist due to the nature of the tropane ring and are especially difficult positions for "branches" necessary for conjugates of the instant invention. One embodiment, adds the "branches" then builds the tropane ring last. As represented in FIG. 15, a novel single step addition of the peroxy radical 2 and cyclization of, at low temperature, general compound 1. The stereochemical outcome is defined by the boat-like form of the intermediate 3 in which addition of the peroxide radical 2 occurs equatorially at position 3 followed by ring closure by the predicted mechanism, which gives the 3β benzoate ester adduct 4 (cocaine analog). The orientation of C, D, E and $CO_2R$ would be predefined in 1.

There is a wide range of compounds which have been developed to facilitate cross-linking of proteins or conjugation of proteins to derivatized molecules, e.g. haptens. These include but are not limited to carboxylic acid derived active esters (activated compounds), mixed anhydrides, acyl halides, acyl azides, alkyl halides, N-maleimides, imino esters, isocyanates and isothiocyanates, which are known to those skilled in the art. These are capable of forming a covalent bond with a reactive group of a protein molecule. Depending upon the activating group, the reactive group is the e amino group of a lysine residue on a protein molecule or a thiol group in a carrier protein or a modified carrier protein molecule which, when reacted, result in amide, amine, thioether, amidine urea or thiourea bond formation. One skilled in the art may identify further suitable activating groups, for example, in general reference texts such as *Chemistry of Protein Conjugation and Cross-Linking* (Wong, Shan, (1991) CRC Press, Inc., Boca Raton, Fla.).

Ideally, conjugation would be via a lysine side chain amino group. Most reagents react preferentially with lysine. An especially suitable carrier is CTB. Native CTB has 9 lysine residues. To determine if conjugated CTB retains its structure and activity, $G_{M1}$ ganglioside binding are assessed.

As described in the Examples, applicants have expressed and purified large amounts of recombinant CTB which, once optimized, are produced in large fermentation batches. Processes for expressing and purifying recombinant protein are know in the art, for example, U.S. Ser. No. 07/807,529, the teachings of which are incorporated herein by reference. For example, CTB is purified by affinity chromatography (Studier et al., *Methods in Enzymol.*, 185:60–79 (1990)), conjugated to cocaine derivatives, and the conjugate is then further purified. Both the purified CTB and the resulting conjugate are analyzed using standard techniques, including SDS-PAGE, N-terminal sequence analysis, Western blotting, mass spectrometry and other analytical techniques to assess the homogeneity of the conjugate. Both the solubility and the stability of the conjugate are optimized in preparation for full-scale formulation.

Several conjugates produced according to the present invention include conjugates with analogs of cocaine and either BSA, HEL or CTB as the protein carrier. In particular, six cocaine analogs have been produced and are shown on FIG. 3. Of the six PS-2, -4, -5, -6, and -9 were conjugated with BSA and HEL. PS-5 was conjugated with CTB. (See Table 2 above)

In order to vary levels of haptenation, alternative approaches are analyzed. In one embodiment the carrier is haptenated with a multivalent cocaine construct. This idea is based on the concept of multiple antigenic peptides (MAP) (Lu et al., *Mol. Immunol*., 28:623–630 (1991)). In this system, multiple branched lysine residues are exploited to maximize hapten density and valency. The premise of this approach is that the immune response is enhanced if there are multiple copies of the hapten attached to the same peptide or protein molecule. Therefore a multivalent hapten which needs to be attached to only one or two sites on the carrier CTB pentamer is prepared as set out herein. The core of such a multiple antigenic hapten is a branched polylysine core as suggested by Tam (Lu et al., supra). A chemically reactive handle is preserved by inclusion of a protected Cys residue. After cocaine haptenation of all available amino groups, the sulfhydryl of Cys is unmasked and made available for coupling to the protein with any of several bifunctional sulfhydryl/amino specific cross-linkers (Yoshitake et al., Physicians Desk Reference, 101:395–399 (1994)). A number of dendrimeric structures are used as a core.

Adjuvant

Initial experiments aimed at demonstrating the feasibility of a therapeutic vaccine against cocaine addiction used the powerful adjuvant CFA (FIGS. 9A and C). However, CFA is not preferred in humans. At present, the only adjuvant currently licensed for use in humans is alum. Preliminary data in the murine model suggests that alum is capable of inducing a strong anti-cocaine antibody response (FIG. 9B). RIBI adjuvant is also suitable. There is a great deal of interest in the development of more powerful adjuvants for use in humans. Accordingly, any adjuvant which does not mask the effect of the carrier is considered useful in the cocaine therapeutic vaccine of the present invention.

Excipients and Auxiliary Agents

Therapeutic compositions may optionally contain one or more pharmaceutically acceptable excipients including, but not limited to, sterile water, salt solutions such as saline, sodium phosphate, sodium chloride, alcohol, gum arabic, vegetable oils, benzyl alcohols, polyethylene glycol, gelatine, mannitol, carbohydrates, magnesium stearate, viscous paraffin, fatty acid esters, hydroxy methyl cellulose, and buffer. Other suitable excipients may be used by those skilled in that art. The therapeutic composition may optionally comprising at least one auxiliary agent, for example, dispersion media, coatings, such as lipids and liposomes, surfactants such as wetting agents and emulsifiers, lubricants, preservatives such as antibacterial agents and anti fungal agents, stabilizers and other agents well known to those skilled in the art. The composition of the present invention may also contain further adjuvants, agents and/or inert pharmacologically acceptable excipients which may be added to enhance the therapeutic properties of the drug or enable alternative modes of administration.

Highly purified hapten-carrier conjugates produced as discussed above may be formulated into therapeutic compositions of the invention suitable for human therapy. If a therapeutic composition of the invention is to be administered by injection (i.e., subcutaneous injection), then it is preferable that the highly purified hapten-carrier conjugate be soluble in aqueous solution at a pharmaceutically acceptable pH (that is, a range of about 4–9) such that the composition is fluid and easy administration exists. The composition also optionally includes pharmaceutically acceptable excipients, adjuvant and auxiliary agents or supplementary active compounds. Depending upon the mode of administration, optional ingredients would ensure desirable properties of the therapeutic composition, for example, proper fluidity, prevention of action of undesirable microorganisms, enhanced bioavailability or prolonged absorption.

A therapeutic composition of the invention should be sterile, stable under conditions of manufacture, storage, distribution and use, and preserved against the contaminating action of microorganisms such as bacteria and fungi. A preferred means for manufacturing a therapeutic composition of the invention in order to maintain the integrity of the composition is to prepare the formulation of conjugate and pharmaceutically excipient such that the composition may be in the form of a lyophilized powder which is reconstituted in excipients or auxiliary agents, for example sterile water, just prior to use. In the case of sterile powders for the preparation of sterile injectable solutions, the preferred methods of preparation are vacuum drying, freeze-drying or spin drying which yields a powder of the active ingredient plus any additional desired ingredient from a previously sterile-filtered solution thereof.

The active compounds of this invention can be processed in accordance with conventional methods of galenic pharmacy to produce therapeutic compositions for administration to patients, e.g., mammals including humans. The preferred modes of administration are intranasal, intratracheal, oral, dermal, and/or injection. One particularly suitable combination of modes of administration comprises an initial injection with intranasal boosts.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound (conjugate) is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments etc., which are, if desired, sterilized or mixed with auxiliary agent. For topical application suitable are sprayable aerosol preparations wherein the active compound, preferably in combination with a suitable excipient or auxiliary agent, is packaged in a squeeze bottle or in admixture with a pressurized volatile, normally gaseous propellant.

When used in the treatment of cocaine, the therapeutic composition contains the hapten-carrier conjugate which has specific characteristics. Cocaine is a relatively small molecule of approximately 300 daltons. An antibody raised through the compositions and methods of the instant invention, would range from 150,000 to 1,000,000, averaging approximately 160,000 daltons. Using the optimized conjugate in the therapeutic composition, after vaccination, upon subsequent exposure, free cocaine will be targeted by the cocaine-specific antibody or antibodies. No changes in the form or structure of the drug are necessary for the antibody to recognize the drug in vivo. While not intending to limit the present invention, it is believed that upon exposure of the vaccinated individual to cocaine, the anti-drug antibodies will block the effects of cocaine. At least three mechanisms are believed to contribute to the blocking activity. First, antibodies are unable to cross the blood-brain barrier. Therefore, it is believed that cocaine, when bound to the anti-cocaine antibody, will not cross the blood-brain barrier and will not be able to exert its effect on dopamine transporters. Second, the antibody prevents the drug from binding to its receptor by simple steric blockade. This mechanism is expected to be operative in blocking some of the non-CNS effects of cocaine (e.g. cardiac toxicity) and in the activity of antibodies against other drugs with non-CNS targets. Third, cocaine has a relatively short half-life in vivo due to both enzymatic and non-enzymatic hydrolysis, creating inactive metabolites. Antibody binding should not affect the rate of non-enzymatic hydrolysis and bound cocaine will rapidly degrade before it has a physiological effect. Cocaine, in particular, is a sufficiently small drug that is unable to cross-link antibodies, thus, no immune complex formation will occur. Further, the drug, unconjugated to a protein carrier, does not affect T cell or B cell activation.

Still further embodiments of mucosal applications are used in the practice of the present invention. For example, copolymer microspheres are used to induce or enhance a mucosal immune response. These small, biodegradable microspheres encapsulate and protect the antigen and facilitate uptake by the mucosal immune system. Although they are most widely used for oral immunization, they also have been reported to be effective with intranasal immunization (Walker, R. I., *Vaccine*, 12:387–399 (1994)). Inert polymers such as poly(lactide-co-glycolide) (PLG) of 1–10 μM diameter appear optimal in this regard (Holmgren et al., *Am. J. Trop. Med. Hyg.*, 50:42–54 (1994), (Serva, R. F., *Science*, 265:1522–1524 (1994)).

In addition to the preferred conjugates, cross-immunization with different conjugates is carried out in order to minimize antibody cross-reactivity. Mice are primed with conjugates, more particularly PS-5 or PS-9 conjugates, and then boosted at day 14 with the reciprocal PS-9 or PS-5 conjugates coupled to the same carrier, BSA. Only the subset of antibody-secreting B cells that recognize both of the cocaine conjugates are maximally stimulated and expanded. It is believed that because the two conjugates differ in their point of attachment to the cocaine molecule, the specificity of the recognition increases. Specificity of the induced antisera is then confirmed by competition ELISA.

Still further, therapeutic compositions containing more than one conjugate stimulate polyclonal antibodies thereby enhancing antibody response upon subsequent challenge.

Dose

Neutralizing antibody responses against pathogens are known to last for years, and it should be possible to achieve a high-titer anti-cocaine antibody response that is maintained for at least a year. Based on values obtained with conventional vaccines, it should be possible to achieve the concentrations of specific antibody required to neutralize cocaine plasma concentrations (1–10 μM); the $LD_{50}$ data in mice, described in the Examples, clearly demonstrates that physiologically relevant neutralizing antibody concentrations can be achieved. Finally, the ability of maternal antibodies to cross the placenta in women addicted to cocaine, and thus protect the fetus, represents a further desirable effect of therapeutic cocaine vaccination. Optimizing therapy to be effective across a broad population is always challenging yet those skilled in the art use a careful understanding of various factors in determining the appropriate therapeutic dose. Further, antibody responses could be monitored using specific ELISAs as set out in the Examples.

Optimal individualization of therapy is assisted by measuring the concentration of drugs in the plasma. Genetic variation in elimination rates, interactions with other drugs, disease-induced alterations in elimination and distribution, and other factors combine to yield a wide range of plasma levels in patients given the same-dose. Clinical indicators assist the titration of some drugs into the desired range, and no chemical determination is a substitute for careful observations of the response to treatment. Because, clearance, half-life accumulation, and steady state plasma levels are difficult to predict, the measurement of plasma levels is often useful as a guide to the optimal dose. Each of the conjugates/carriers/adjuvants of the present invention is evaluated for the ability to induce an antibody response that is best able to bind free cocaine in the circulation. Thus, it will be appreciated that the actual preferred amounts of active compound in a specific case will vary according to the specific conjugate being utilized, the particular compositions formulated, the mode of application, and the particular situs and organism being treated. For example, in one embodiment, the therapeutic composition containing a suitable carrier, is given first parenterally and boosted mucosally . As is discussed in more detail herein, this type of immunization with the optimal hapten and carrier combination is very effective in generating primarily IgG systemically and primarily IgA locally.

In one cocaine specific therapeutic composition of the instant invention, 4 mg cocaine-specific antibody (mAb) blocks the effects of a molar excess of cocaine (1 mg/kg.;≈300 μg/rat) in a rat addiction model (weight ratio of mAb/cocaine≈ 160,000/303=500). This represents an attainable level in vaccine response; ca. 100 μg/ml in rat system, equivalent to 1% total antibody. Although estimates vary, the typical cocaine dose for addicts is in the 25–100 mg range. Higher levels (>200 mg) can be used by hardened addicts (especially i.v.) assuming 100% gets in blood stream. This could give 5–20 μg/ml, but due to absorption and tissue distribution, measure peak plasma levels of cocaine in addicts are 0.3–1.5 μg/ml. That is., ca 100×difference in weight of Ab, or close to molar equivalence. Confirmation of the predicted relationship of antibody levels and cocaine dose predicted is achieved by comparison with passively transferred antisera.

Although other methods of calculating appropriate dosage are well known to those skilled in the art, without intending to limit the invention, one method of predicting anti-cocaine antibody titer requirements is disclosed. For purposes of this calculation, an approximately equimolar ration of antibody is desired. For example, 1–6 μM antibody would equal 160–960 μg/ml specific antibody. A desired specific antibody response is about 1% to about 5% total Ig or about 100 to about 500 μg/ml. Further the affinity of the antibody must be taken into consideration. "Affinity" reflects the amount of antibody-drug complex at equilibrium, thus:

$K_A$=[Ab–drug complex]/[Ab]=[drug]

where [Ab]=molar concentration of unoccupied ab binding sites

[drug]=molar concentration of unoccupied (by ab) cocaine sites

[Ab–drug]=molar concentration of Ab-drug complex sites occupied on Ab=$K_A$×c/1+$K_A$c where c=concentration of Ab Thus based on calculations, the affinity required for a 1:1 Ab to drug binding ratio as described, requires an antibody with an affinity of approximately $10^{-7}$M. At least one commercially available anti-cocaine monoclonal antibody has an approximate affinity of 100 nM. However, by inducing a pentameric IgA response in the mucosa as disclosed in at least one embodiment herein, the antibody to drug ration is five times less with a subsequent decrease in affinity of antibody required.

To prove efficacy of the therapeutic vaccine, addiction models in experimental animals are used, for example, a drug discrimination model in the rat. (Woods et all, *Clin. & Behav. Aspects*, 21:65 (1987)), and (Witkin, *J. M., Neurosci. and Biobehav. Reviews*, 18:121–142 (1994)). Rats are trained to press a particular lever upon receiving an injection of cocaine. The animals indicate whether they have received an injection of cocaine or of saline by pressing different levers. A quantitative and reproducible measure of whether the animals can detect a given dose of cocaine can be determined by measuring how many times the rats press the correct lever. The ability of cocaine to induce the correct response is termed the discriminative stimulus property. If the anti-cocaine antibodies induced by the therapeutic vaccine are effective at neutralizing the physiological effects of the cocaine, the rats require a much larger dose of cocaine to stimulate a response on the cocaine lever. The activity of cocaine in this system has been shown to positively correlate with the subjective effects of drugs in human subjects (Witken et al., supra) and (Holtzman, S. G., *Modern Meth. in Pharmacol*, 6:193–210 (1990)). This model is more labor-intensive than measurement of the cocaine $LD_{50}$, however, it has the advantage that relatively low doses of cocaine can be detected. These data provide a sensitive and quantitative measure of the efficacy of the therapeutic vaccine in vivo.

As set out in the Examples murine models have been used to demonstrate and measure four different characteristics of the antibody response, that is, (1) antibody titer, (2) ability to recognize free cocaine, (3) specificity of antibody response and (4) the physiological effects of cocaine ($LD_{50}$).

Antibody titer

The first screen for the vaccination is to determine whether the conjugate of interest induces a high titer antibody response. Antibody titers are determined using an ELISA assay as described in the Examples below. Plates are coated with a cocaine-HEL conjugate, washed extensively, and incubated with varying dilutions of the test serum. The plates are again washed and developed with an enzyme-labeled anti-mouse Ig second antibody. Titers are defined as the reciprocal of the dilution of serum that gives 50% of the maximal response.

Ability to recognize free cocaine

Once a conjugate is capable of inducing a high-titer serum antibody response, the serum also is tested for its ability to recognize free cocaine in a competition ELISA as described in the Examples. An ELISA assay is set up using a suboptimal dilution of serum. Varying concentrations of free cocaine are added along with the antiserum, and the ELISA is developed as above. Data is expressed as the concentration of free cocaine required to compete 50% of the antibody binding, an approximate measure of affinity. Lidocaine, among others, is used as a negative control in the competition experiments, and the cocaine-protein conjugate that was used in the immunization is used as a positive control.

In addition to the competition ELISA assay binding is assessed using radiolabeled cocaine. The data resulting from such assays can indicate if the immune serum is binding to free cocaine. This is discussed in more detail in the Examples.

Specificity of antibody response

In order to be maximally effective at blocking the activity of cocaine, the induced antibodies must have minimal affinity for inactive metabolites of cocaine. Binding of antibodies to pharmacologically inactive metabolites of cocaine would reduce the potency of the vaccine. The primary inactive metabolites are ecgonine methyl ester, norcocaine and benzoylecgonine each of which is commercially available. The specificity of the antisera for each of these metabolites is determined in a competition ELISA and by radiolabeled immunoassay.

Additionally, interaction of the antibodies raised with other drugs used in addiction therapy and in other medical procedures should be minimized. In particular, cross reaction with drugs commonly prescribed to cocaine and poly drug abusers is avoided. While the unique nature of the cocaine tropane ring structure minimizes cross-reactivities, they can be readily tested in a competition ELISA. Indeed, lidocaine is used as a negative control in our competition ELISA. The following molecules are useful as co-treatments, buprenorphine, desipramine, naloxone, haloperidol, chlorproazine, and bromocriptine, as well as others that may become relevant.

Effect on cocaine $LD_{50}$

Those conjugates and immunization protocols that are most effective at inducing high titer specific antibody responses are further evaluated for their ability to shift the cocaine $LD_{50}$. These experiments are carried out as described herein. Cocaine-immunized and control carrier-immunized mice are injected i.v. with cocaine at doses around the previously defined $LD_{50}$. Ten mice are used at each point, and the data is analyzed using a Cochran-Mantel-Haenzel Chi-squared test.

In addition, a failure time model will be used to analyze the time-to-death induced by cocaine. The extent to which the anti-cocaine antibodies increase both (a) the dose of cocaine required for lethality and (b) the time-to-death are measures of efficacy in this model. These provide a rapid and rigorous test of the in vivo efficacy of the antibodies.

Observing the Physiological Effect on Humans

A person who seeks medical attention during an episode of abuse might present with a rapid pulse, an increased respiratory rate and an elevated body temperature. At high levels of overdose, the picture progresses to grand mal convulsions, markedly elevated blood pressure, and a very high body temperature, all of which can lead to cardiovascular shock. In addition to blood levels, all these factors will be assessed and specific criteria will be established when administration of either active immunization with the vaccine or passive administration of antibodies to humans is contemplated.

When embodiments of the invention were tested on mice, immunization with a protein-cocaine conjugate induced an antibody response that shifts the $LD_{50}$ for cocaine (FIG. 11 A & B). It is hypothesized that the relatively small shift that was observed at very high doses of cocaine translates into a more dramatic shift at lower cocaine concentrations; the dramatic effect of the anti-cocaine mAb on cocaine self-administration is consistent with this hypothesis.

Without intending to limit the scope of the invention, the composition and methods of this invention will now be described in detail with reference to a preferred drug of abuse, cocaine, and specific embodiments.

Unless otherwise indicated in the Examples, female BALB/c mice of 2–3 months of age are used in these studies. These animals have a well defined reproducible response to the antigens under investigation. Animals are immunized either subcutaneously, intratracheally, or intranasally with a protein-cocaine conjugate either in saline or in alum. Unless otherwise noted, BALB/c mice are immunized s.c. with 50 μg of test conjugate. After 14 days, mice are boosted with the same dose. Antibody responses in the serum are measured after an additional 14 days. Five mice are used per group and all sera are tested individually.

It is to be understood that the example and embodiments described herein are for purposes of illustration only, and that various modification in light thereof will be suggested to persons skilled in the art. Accordingly, the following non-limiting Examples are offered for guidance in the practice of the instant invention.

EXAMPLE 1

Synthesis of PS-2

A solution of ecgonine methyl ester hydrochloride (50 mg., 0.21 mmol), diisopropylethylamine (80 μl, 0.46 mmol) in DMF (3 ml) was treated with bromoacetyl bromide (22 μl, 0.25 mmol) and heated at 40° C. overnight. The solvents were removed under reduced pressure and the residue purified by silica gel flash chromatography (9:1 chloroform-:methanol as the eluent), furnishing the bromo compound (67 mg, 96%) as a pale yellow powder.

To a solution of-the bromo compound (17 mg, 0.053 mmol) in PBS (0.5 ml), thiolated BSA (15 mg) in PBS (0.5 ml) was added and stirring continued at ambient temperature for 3 days. The conjugate was purified by dialysis against PBS and then analyzed by mass spectral analysis.

EXAMPLE 2

Synthesis of PS-4

To a solution of ecognine methyl ester (32 mg, 0.16 mmol) in DMF (2 ml), triethylamine (22 μl, 0.16 mmol), followed by succinic anhydride (16 mg, 0.16 mmol) was added and the solution heated at 35 ° C. for 2 hours. The solvent was removed under reduced pressure and the residue purified by silica gel flash chromatography (9:1 chloroform-:methanol as the eluent). This furnished the desired hemisuccinate (21 mg, 44%) as a white powder.

To a solution of the hemisuccinate (2.4 mg, 7.69 µmol) in distilled water (0.5 ml) at 0° C., EDC (1.5 mg, 7.69 µmol) was added. After 10 minutes, BSA (2 mg in 0.5 ml PBS) and the solution allowed to warm to ambient temperature overnight. The conjugate was purified by dialysis against PBS and the degree of haptenation determined by mass spectral analysis.

EXAMPLE 3

Figure 7:
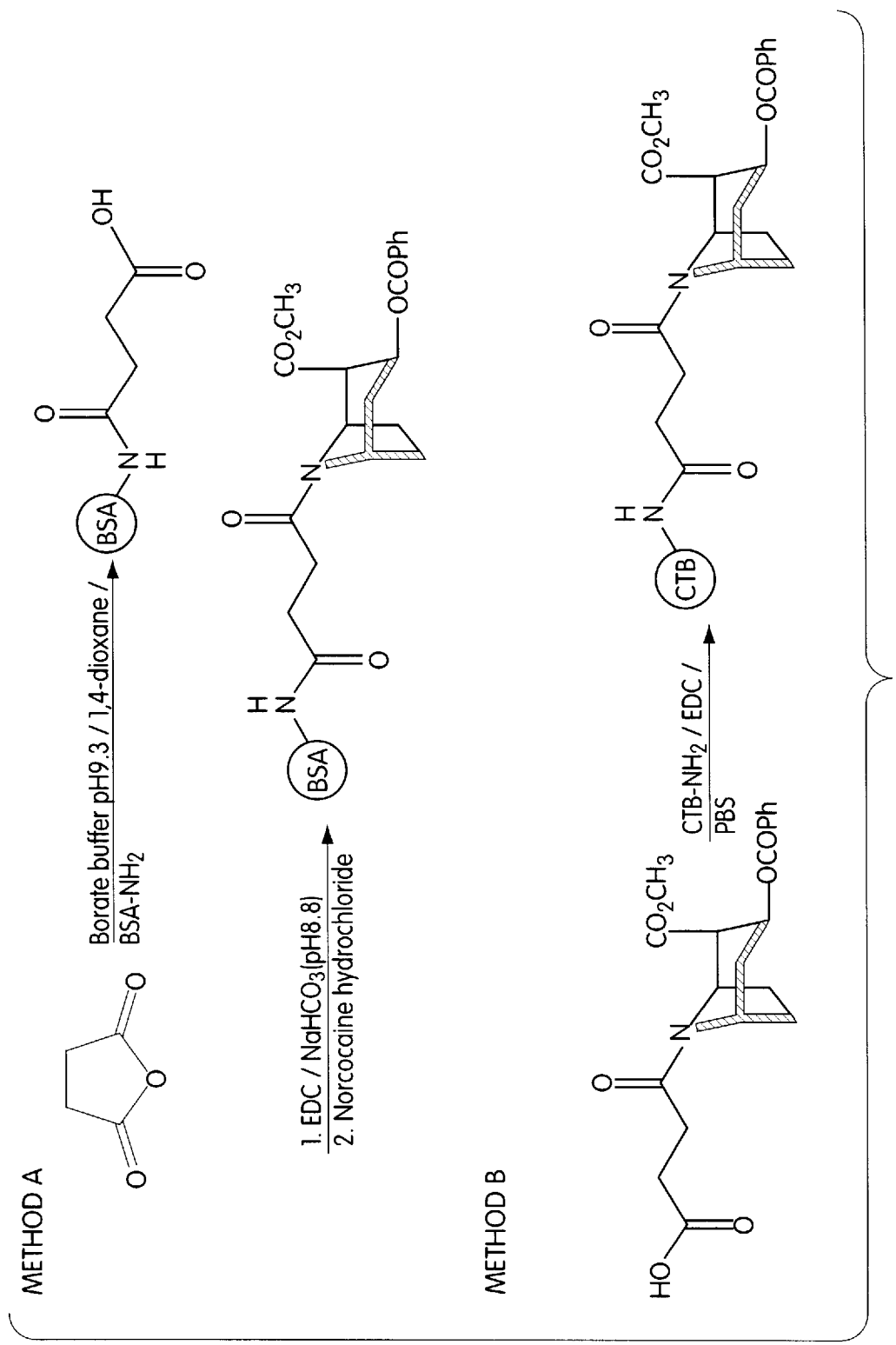
FIG. 7 is a schematic diagram representing two possible conjugation reactions to prepare a single cocaine conjugate (PS-5) according to the methods of the instant invention.
Figure 8:
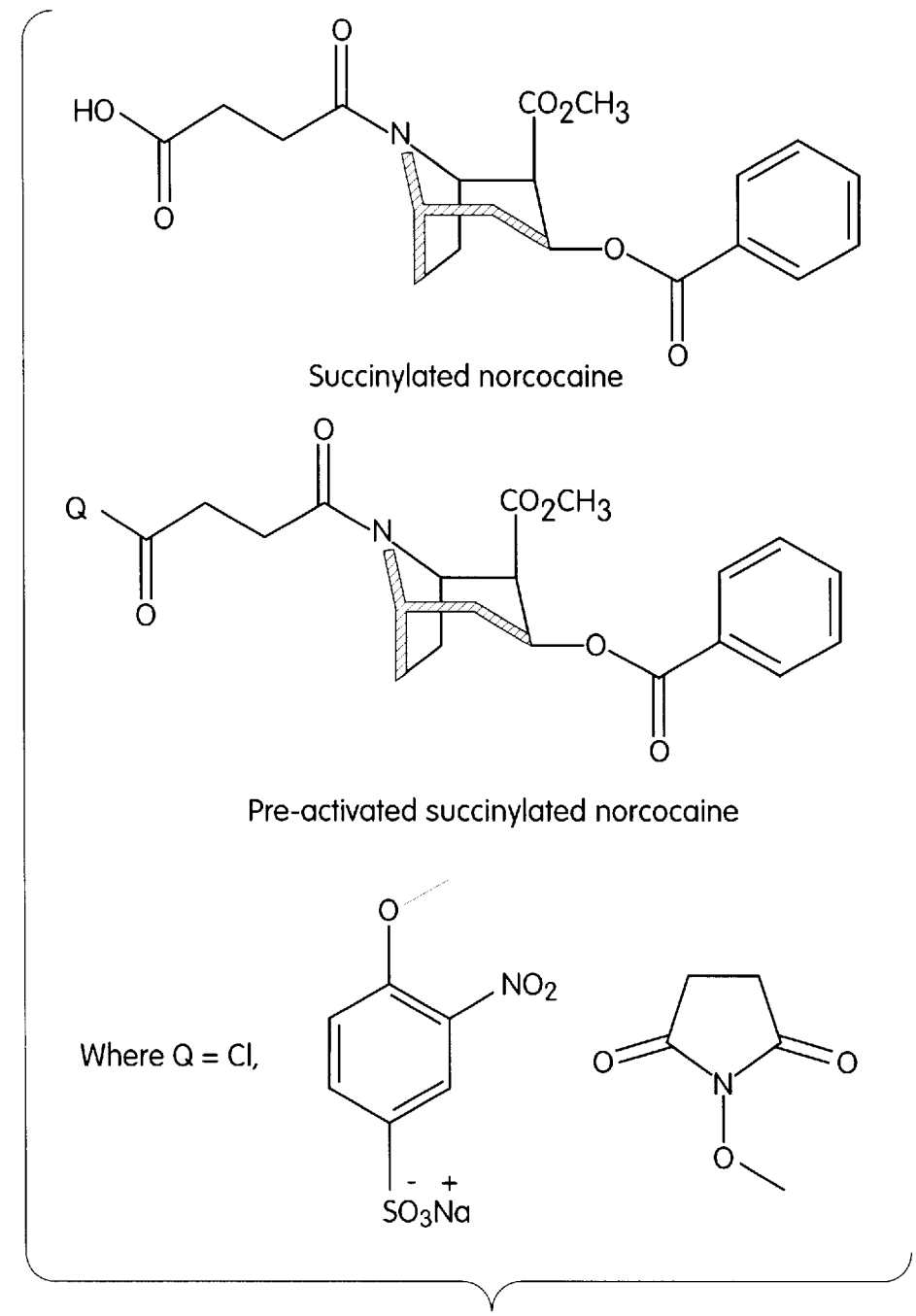
FIG. 8 is a representation of the structures of "succinylated norcocaine" and "preactivated succinylated norcocaine" useful in the preparation of some of the conjugates of the instant invention.

Synthesis of PS-5 (see FIG. 7)

Method A

A solution of norcocaine hydrochloride (1 g, 3.07 mmol), triethylamine (0.86 ml, 6.14 mmol) in DMF (20 ml) was treated with succinic anhydride (614 mg, 6.14 mmol) and the mixture heated at 45° C. overnight. The solvents were removed under reduced pressure and the residue purified using silica gel flash chromatography (2:1 chloroform-:methanol as the eluent). This gave the desired acid (1.0 g, 84%) as a thick syrup.

To a solution of the acid (14 mg. 0.036 mmol) in distilled water (1 ml) at 0° C., EDC (10.4 mg, 0.055 mmol) was added. After 5 minutes a solution of BSA (14 mg) in PBS (1 ml) was added dropwise and the mixture allowed to warm to ambient temperature overnight. The conjugate was purified by dialysis against PBS and the degree of conjugation analyzed by mass spectral analysis.

Method B

To a solution of BSA (500 mg) in 0.2M borate buffer (80 ml), succinic anhydride (270 mg, 2.70 mmol) in 1,4-dioxame (10 ml) was added in 200 µl aliquots over 30 minutes. The pH was maintained at 9.3 by addition of 3N sodium hydroxide solution. The solution was kept at ambient temperature for 18 hours, dialyzed against 0.01M triethylamine and then lyophilized to yield 583 mg of a fluffy white powder. Mass spectral analysis of the product indicated 55 succinoyl groups per BSA molecule.

A solution of succinylated BSA (72 mg) in 0.1M sodium bicarbonate buffer, pH 8.8 (15 ml) at 0° C. was treated with EDC (88 mg, 0.46 mmol). After 5 minutes, norcocaine hydrochloride (100 mg, 0.31 mmol) was added and the solution allowed to warm to ambient temperature overnight. The conjugate solution was purified by dialysis against PBS and the degree of haptenation determined by mass spectral analysis.

EXAMPLE 4

Synthesis of PS-6

To a solution of benzoyl ecgonine (276 mg, 0.96 mmol) in DMF (5 ml) at −10° C., borane-dimethylsulfide complex (1.0M solution in methylene chloride; 1.0 ml, 1.01 mmol) was added dropwise. This was allowed to warm to ambient temperature overnight, after which the reaction was quenched by the addition of THF: water (1:1 ratio v/v) followed by stirring for a further 10 minutes. The solvents were removed under reduced pressure and the residue purified using silica gel flash chromatography ( chloroform followed by methanol as eluents). This furnished the desired alcohol (246 mg, 93%) as a white powder.

To a solution of the alcohol (190 mg, 0.69 mmol) in DMF (5 ml), triethylamine (0.19 ml, 1.38 mmol) was added, followed by succinic anhydride (138 mg, 1.38 mmol) and heated at 40° C. overnight. The solvents were removed under reduced pressure and the residue purified using silica gel flash chromatography (1:1 chloroform: methanol as the eluent). This furnished the hemisuccinate (123 mg, 48%) as a white powder.

To a solution of the hemisuccinate (16 mg, 0.043 mmol) in distilled water (0.5 ml) at 0° C., EDC (12 mg, 0.064 mmol) was added. After 5 minutes, BSA (16 mg) in PBS (0.5 ml) was added dropwise and the solution allowed to warm to ambient temperature overnight. The conjugate solution was purified by dialysis against PBS and the degree of haptenation determined by mass spectral analysis.

EXAMPLE 5

Synthesis of PS-9

To a solution of benzoyl ecgonine (10 mg, 0.035 mmol) in distilled water (1.0 ml) at 0° C., EDC (10 mg, 0.052 mmol) was added. After 5 minutes BSA (10 mg) in PBS (0.5 ml) was added dropwise and the solution warmed to ambient temperature overnight. The protein conjugate was purified by dialysis against PBS buffer. The degree of haptenation was determined by mass spectral analysis.

EXAMPLE 6

Synthesis of CTB-PS-5

To a solution of succinylated norcocaine (2 mg, 5.14 µmol) in DMF (0.5 ml), diisopropylethylamine (1 µl 5.14 µmol) was added followed by HATU (2 mg, 5.40 µmol). After 10 minutes the pale yellow solution was added dropwise to a solution of CTB (1 mg in 2 ml of distilled water) and then kept at ambient temperature for 2 days. The conjugate solution was purified by dialysis against PBS and the degree of haptenation measured by mass spectral analysis.

EXAMPLE 7

A solution of succinylated norcocaine (15 mg; 0.39 µmol), thionyl chloride (28 µl, 0.39 mmol) in DMF (250 µl) was stirred at ambient temperature for 2 hours. After the reaction was deemed complete (by TLC analysis), the solvents were removed under reduced pressure and the resulting chloro derivative taken through to the next step without further purification.

The chloro derivative (16 mg, 0.04 mmol) was dissolved in DMF (100 µl) and added dropwise to a solution of CTB (0.38 mg/ml in 3 ml PBS). The resulting mixture was kept at ambient temperature overnight, dialyzed against PBS and the degree of haptenation determined by mass spectral analysis.

EXAMPLE 8

To a solution of succinylated norcocaine (100 mg, 0.26 mmol) in DMF (5 ml), DCC (64 mg, 0.31 mmol) was added. After 10 minutes, 4-hydroxy-3-nitrobenzene sulfonic acid sodium salt (74 mg, 0.31 mmol) was added and the resulting yellow solution kept at ambient temperature for 4 days. The resulting suspension was filtered under reduced pressure and the filtrate added to cold diethyl ether (10 ml) with vigorous stirring. Hexane (5 ml) added and after complete precipitation of a yellow oil, the colorless supernatant was decanted off. This process was repeated and the oil dried overnight under reduced pressure, furnishing the desired ester (157 mg) which was taken through to the next stage without further purification.

The ester (5 mg, 8.16 $\mu$mol) was dissolved in DMF (100 $\mu$l) and added dropwise to CTB (1 mg in 2 ml PBS) at 4° C. and then warmed to ambient temperature. After 3 hours the conjugate solution was purified by dialysis against PBS and the degree of haptenation determined by mass spectral analysis.

EXAMPLE 9

To a solution of succinylated norcocaine (108 mg, 0.28 mmol) in DMF (5 ml) at 0° C., NMM (37 $\mu$l, 0.33 mmol) followed by ethyl chloroformate (32 $\mu$l, 0.33 mmol) were added. After 10 minutes, N-hydroxysuccinimide (38 mg, 0.33 mol) was added and the solution warmed to ambient temperature over 18 hours. The solvents were removed under reduced pressure and the reside recrystallized from isopropanol/diethyl ether to furnish the N-oxysuccinimidyl ester (113 mg, 84%) as a white powder.

A solution of the ester (2 mg, 4.11 $\mu$mol) in DMF (100 $\mu$l) was added dropwise to a solution of CTB (1 mg in 2 ml PBS). After 3 days the conjugate solution was purified by dialysis against PBS and the degree of haptenation determined by mass spectral analysis.

EXAMPLE 10

To a solution of norcocaine hydrochloride (50 mg, 0.15 mmol) in DMF (1 ml), diisopropylethylamine (27 $\mu$l, 0.31 mmol) was added. After 5 minutes the solution was cooled to 0° C. and added dropwise to a solution of adipoyl chloride (44 $\mu$l, 0.080 mmol) in DMF (100 $\mu$l) at 0° C. After 2 hours the solution was added dropwise to a solution of CTB (1 mg in 2 ml PBS) at 0° C. and warmed to ambient temperature overnight. The conjugate solution was purified by dialysis against PBS and the degree of haptenation determined by mass spectral analysis.

EXAMPLE 11

MAP Resin (Substitution level: 0.48 mmol/g; 50 mg, 0.023 mmol) was pre-swollen in DMF (5 ml). The solvent was decanted and the resin treated with a solution of 20% piperidine in DMF (5 ml), agitated for 15 minutes and the solvents removed by decanting. The resin was washed sequentially with DMF (5 ml), methanol (5 ml) and DMF (5 ml). a solution of succinylated norcocaine (18 mg, 0.046 mmol) in DMF (1 ml) was treated with a mixture of HOBt/DMF/HATU (0.5M freshly prepared solution in DMF; 92 $\mu$l, 0.046 mmol) and after 5 minutes, this was agitated overnight after which the reaction was deemed to be >90% complete by the Kaiser-Ninhydrin test. The solvents were decanted off and the resin beads washed exhaustively with methanol, followed by drying under a stream of argon. The derivatized MAP was cleaved by suspending the resin in 2.5% phenol/TFA/EDT (5 ml) and agitating for 1 hour, filtered, washed with TFA (4×4 ml) and the solvents removed under reduced pressure. The crude peptide was triturated with cold diethyl ether, centrifuged for 5 minutes at 5000 rpm and the process repeated. The pellet was dissolved in water and lyophilized to give 1 mg of crude peptide.

EXAMPLE 12

Synthesis of (N-succinamidylcocaine)$_8$ -MAP protein conjugate Synthesis of the non-hapten portion (MAP core)

Synthesis of the non-hapten portion (MAP core) of the poly-haptenated MAP shown in FIG. 1 is carried out by manual peptide synthesis as described by Tam et al (U.S. Pat. No. 5,229,490). Amino groups are protected by the Boc (t-butyloxycarbonyl) function and the sulfhydryl group of Cys is protected as its 3-nitro-2-pyridylsulfenyl (npys) derivative.

After assembly on the resin and removal of Boc protecting groups with TFA as described by Tam (supra.), the MAP core is cleaved from the resin by HF cleavage leaving the Npys group intact.

Crude MAP core is taken up in 7M guanidine hydrochloride containing 0.2M HOAc and subjected to gel permeation chromatography in 0.2M HOAc on Sephadex G-10 t remove any remaining low molecular byproducts generated by the HF cleavage. The MAP core is lyophilized from 0.2M HOAc.

Preparation of (N-succinamidyl-norcocaine)$_8$-MAP

See Example 11

Coupling of (N-succinamidyl-norcocaine)$_8$ MAP to carrier

Prior to coupling to activated protein the thiol group is exposed by treatment with a molar equivalent of tris-(2-carboxyethyl) phosphine hydrochloride (TCEP). Activated protein carrier is dissolved at 5 mg/ml in 0.2M sodium bicarbonate buffer at room temperature. To this solution is added a 2-fold molar excess of (N-succinamidyl-norcocaine) $_8$-MAP at 5 mg/ml. The reaction is allowed to proceed for 20 hours at room temperature and then dialyzed overnight against 0.2M HOAc and lyophilized.

EXAMPLE 13

Testing the Induction of Cocaine Specific Antibody Response

In order to induce an antibody response against a small molecule or hapten, such as cocaine, it is necessary to link it to a protein carrier. The carrier is recognized by T cells which provide help to the cocaine-specific B cells for initiation and maintenance of sustained antibody production. In this example, the carrier used was bovine serum albumin (BSA), a protein which has 36 lysine residues that are exposed and available for conjugation. A panel of structurally distinct cocaine-protein conjugates were produced that were linked through different regions of the cocaine molecule (FIGS. 1a, 1b, 2a, 2b). It was necessary to synthesize a set of conjugates because the cocaine molecule is physically altered and differently oriented during the conjugation process to the carrier. Since any given cocaine conjugate will induce antibodies which recognize the conjugate only, and not the free hapten (cocaine) itself, screening was performed.

Figure 9A:
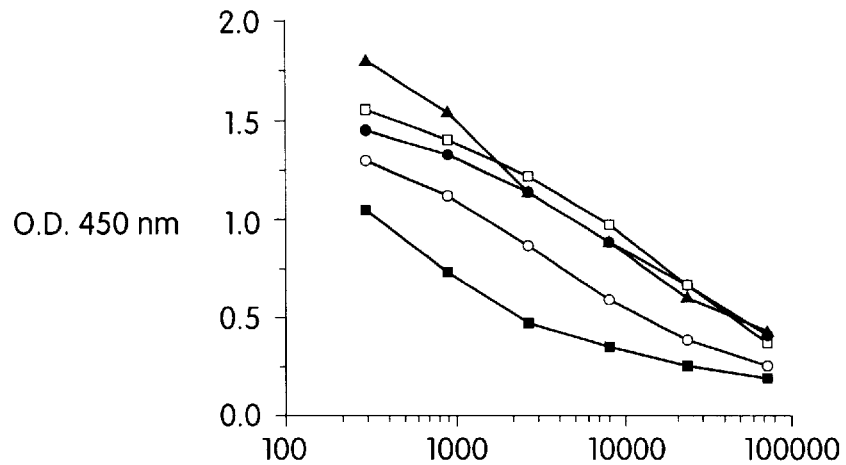
FIGS. 9A, B and C are graphs showing the IgG antibody response in mice immunized with cocaine conjugates of the instant invention. The antibody response is detected by in vitro binding to the appropriate HEL conjugate made using HEL rather than BSA as a carrier. Mice received 2 injections of 50 µg per injection. The curves represent the response of 5 individuals mice per group.
Figure 9B:
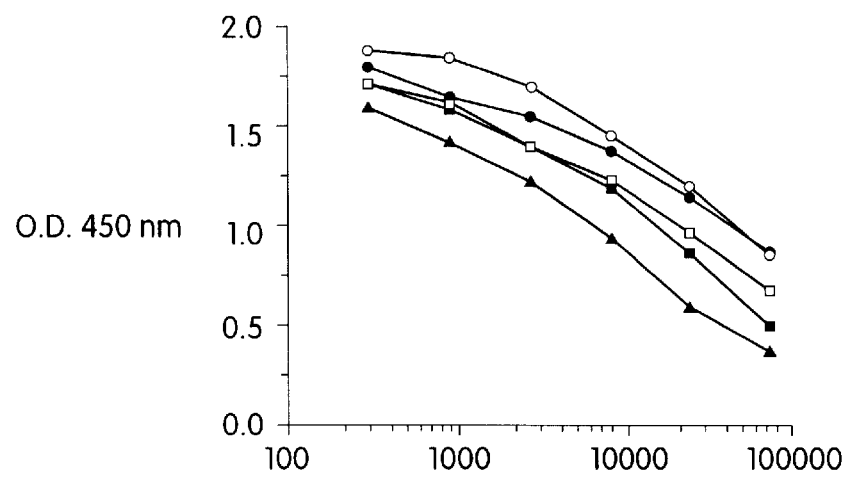
FIG. 9B mice were immunized with PS-5.5 Alum I.p.
Figure 9C:
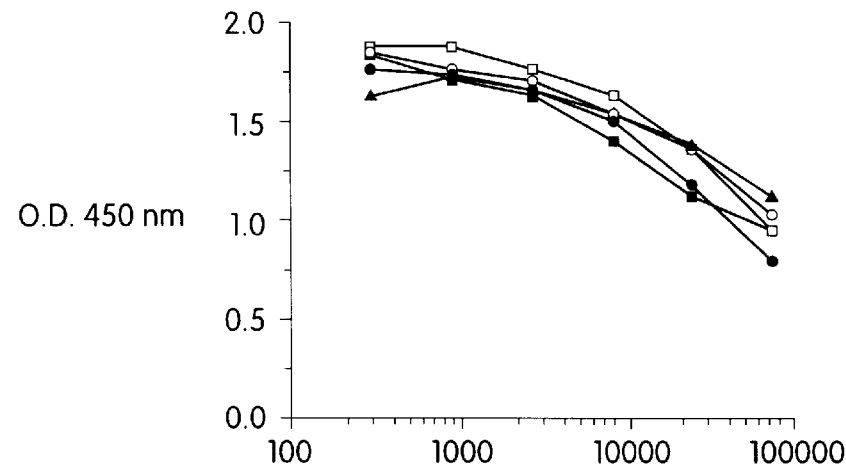
FIG. 9C mice were immunized with PS-9.2+CFA I.p.
Figure 10A:
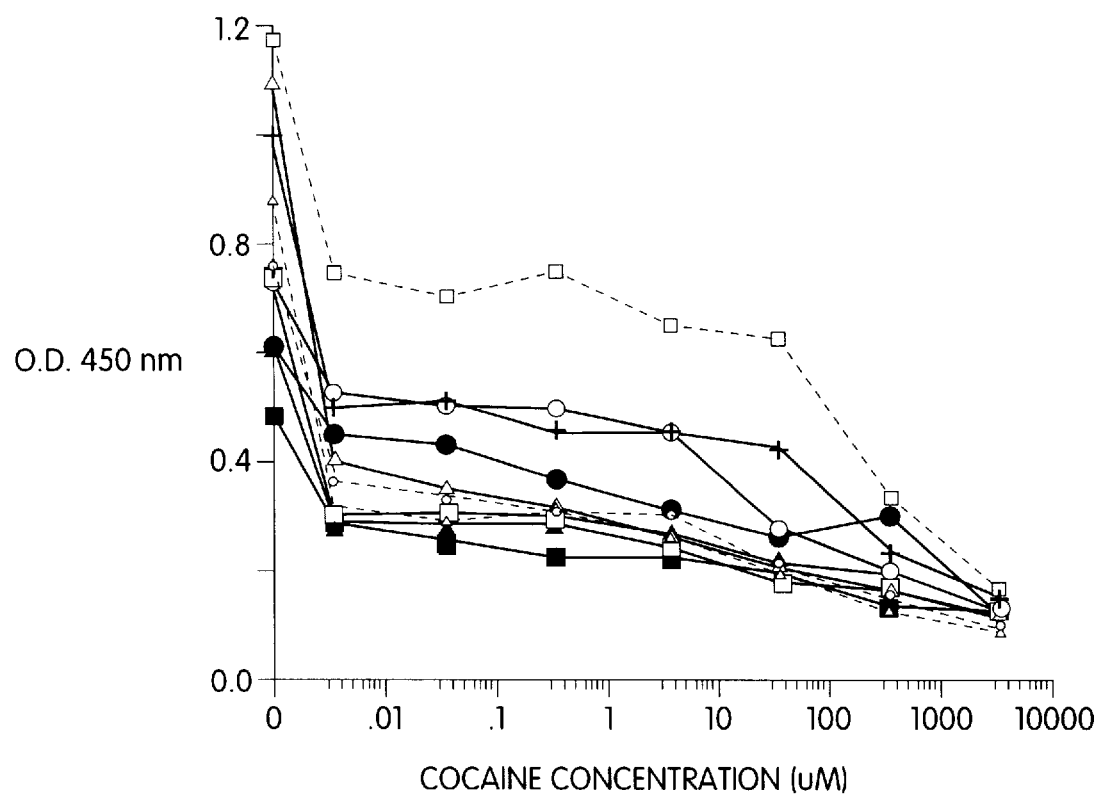
FIGS. 10A and 10B are graphs showing the ability of antiserum from mice immunized with a cocaine-BSA conjugate to bind free cocaine
Figure 10B:
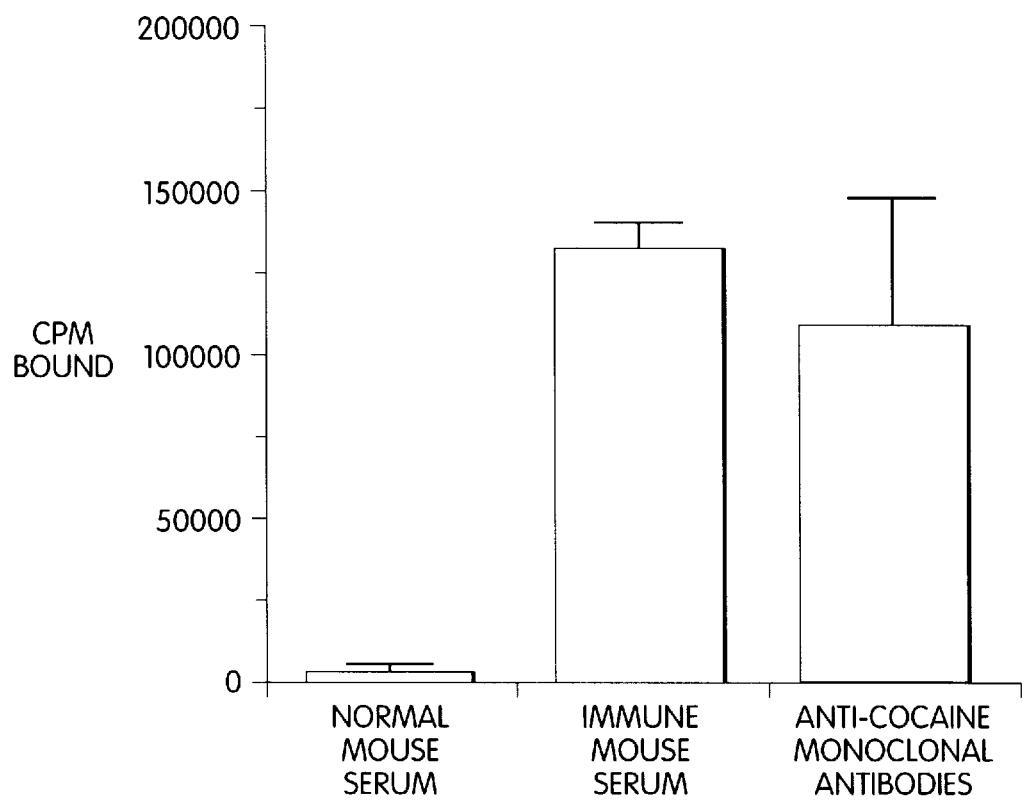

Mice were immunized with 50 $\mu$g of cocaine-BSA conjugate PS-5 (FIGS. 9A and B) or with PS-9 (FIG. 9C) i.p. either with CFA (FIGS. 9A and 9C) or with alum (FIG. 10B). Mice were boosted one time and then bled. Sera were tested in an ELISA assay using plates coated with PS-5 (conjugated to HEL) or PS-9 (conjugated to HEL) as appropriate. The responses of 5 individual mice per group are shown. These data demonstrate that the cocaine-BSA conjugates are able to induce high titer antibody responses.

EXAMPLE 14

Recognition of free cocaine

To directly determine whether the induced antibodies were capable of recognizing the free cocaine molecule, a competition ELISA was established. Plates were coated with appropriate free cocaine-HEL conjugate and incubated with the antisera at a 1:2000 dilution in the presence of varying concentrations of free cocaine as competition. Some conjugates tested failed to induce antibodies that also recognized cocaine itself (data not shown). However, when PS-5-BSA was used as the immunogen, the majority of the antibody response was effectively competed by free cocaine (FIG. 10A and B). In this set of sera from ten mice, (each line on the graph in FIG. 10A indicates a different mouse) one was less effective in the competition assay (open circles) and this mouse was not used in the $LD_{50}$ experiments described herein. The PS-9-BSA conjugate also has been able to induce cocaine-specific antibodies. These data demonstrated that cocaine-carrier conjugates can be synthesized which induce high-titer, cocaine-specific antibody responses that should be capable of neutralizing cocaine in vivo.

EXAMPLE 15

Ability of vaccination to protect against cocaine toxicity

The present invention discloses a cocaine-protein conjugate that induced an anti-cocaine antibody response in a mouse model. These anti-cocaine antibodies neutralized cocaine in vivo, significantly shifting the dose of cocaine required to induce a lethal response in mice.

The efficacy of therapeutic vaccination against cocaine was assessed by determining the lethal dose of cocaine ($LD_{50}$) in immunized and naive animals. The prediction was that a strong cocaine-specific antibody response should bind sufficient quantities of cocaine to prevent the rapid cardiac, respiratory, and neurological effects of cocaine, thus increasing the $LD_{50}$ of cocaine in the immunized mice. Sixty BALB/c mice were immunized with 50 μg PS-5-BSA in CFA and boosted only once with the same conjugate in IFA. Each of the mice was bled at days 24 and 35 and serum antibody titers and competition with cocaine were assessed. Forty-eight mice were chosen for the experiment, with average titers of 18,700, all of which displayed competition with free cocaine. For the $LD_{50}$ experiment, 4–6 mice were used per group and each group was carefully matched for antibody titer and apparent affinity for free cocaine.

Figure 11A:
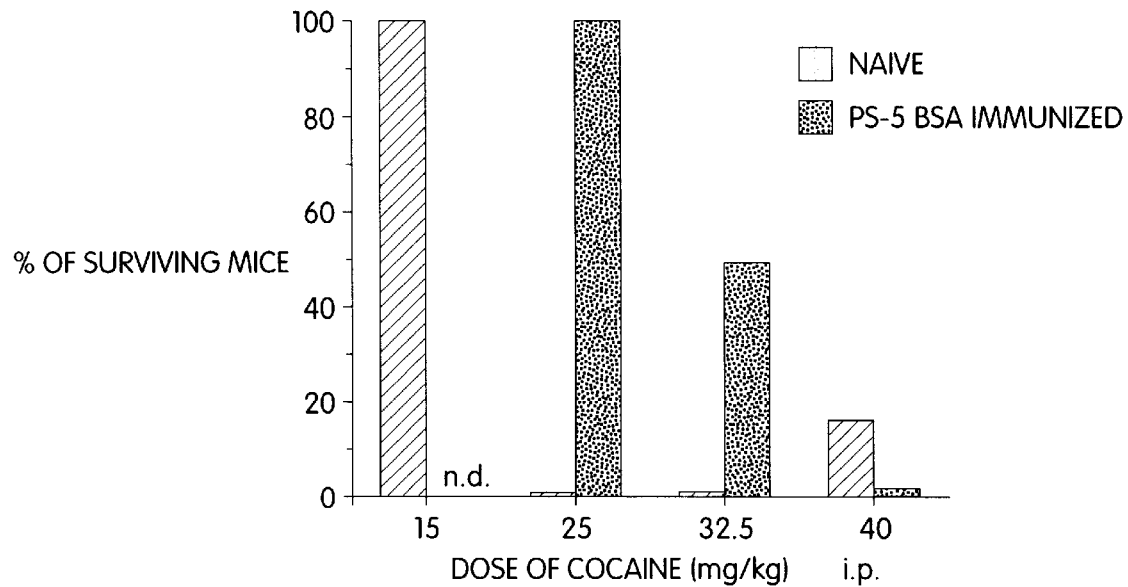
FIGS. 11A and B is a bar graph illustrating that a cocaine-BSA conjugate prepared according to the method of the instant invention provide two-fold protection in high dose cocaine $LD_{50}$.
Figure 11B:
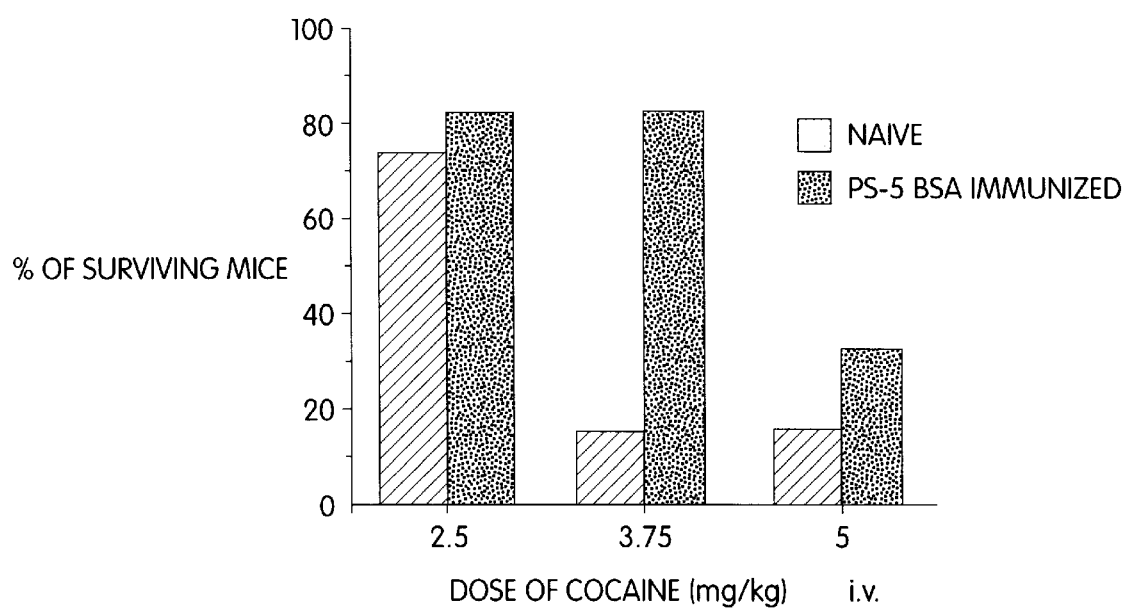

As shown in FIG. 11, the $LD_{50}$ for cocaine in naive BALB/c mice was 3 mg/kg when the drug was given intravenously (i.v., FIG. 11b) and 20 mg/kg when given intraperitoneally (i.p., FIG. 11A). Immunization of mice with the cocaine-protein conjugate changed the $LD_{50}$ significantly. The doses required for half-maximal toxicity were 4.5 mg/kg and 35 mg/kg for the i.v. and i.p. doses, respectively. These doses were significantly different from the value obtained in the naive mice (p=0.048 for i.v. and p=0.014 for i.p., Cochran-Mantel-Haenszel Chi-squared test). The almost two-fold protection of acute high dose toxicity by cocaine vaccination compares favorably with some drugs affecting cocaine pharmacology. For example, the NMDA antagonist MK-801 increased the $LD_{50}$ 1.3-fold and 1.4-fold when combined with propanolol (Itzhak et al., J. of Pharmacol. and Exp. Therap., 262:464–467 (1992)). In addition, vaccination significantly prolonged the time to death from an average of 3.2 min to 5.4 min. for i.v. administration (p=0.007, Wilcoxon 2-sample test) and from 4.0 min to 8.5 min. for i.p. administration (p=0.0003). Although the statistical analysis of the time to death ignores the surviving mice (analysis in a failure-time model would require a larger group size), it does serve to clearly demonstrate that the antibody affected the in vivo physiological response to high dose cocaine.

The first experiments in the rat self-administration system were performed with the anti-cocaine monoclonal antibody (mAb) MO240 that was passively administered to the rats. Initial experiments using an ELISA for an isotype-matched control antibody of irrelevant specificity established that the half-life of the mAb was 4–6 days, sufficiently long to carry out these experiments.

Two rats, responding under the FR 5:FI 5 min schedule of cocaine delivery, were passively administered 4 mg of the mAb specific for cocaine. The antibody was given i.v., and the effect was assessed in a series of daily 2 hr sessions that began 24 hr after mAb administration. If the anti-cocaine mAb had neutralized cocaine in vivo, the rats would increase both response rate and number of cocaine infusions to achieve the desired physiological effect of cocaine. If there was complete blockade by the anti-cocaine mAb, the cocaine would produce little or no physiological effect and the treated rats would gradually extinguish cocaine self-administration.

Additionally, tests have been done which show that a mAb significantly altered the response of the rats to cocaine (data not shown). In the absence of the mAb, the rats maintained a stable baseline response over 6 days. Rats that received the mAb continued to self-infuse cocaine at the next test session, but then extinguished both the rate of response and the number of infusions over 6 days. The pattern of response in the treated rats was comparable to that seen when saline was substituted for cocaine ("x"es). Full recovery to FR 5:FI 5 min baseline performance was achieved after 20 days (not shown), a time when most of the passively administered antibody should have been cleared from the circulation based upon observation of an isotype matched control mAb in rats. These results support the conclusion that an anti-cocaine antibody could completely block the effect of 1 mg/kg infusion of cocaine.

EXAMPLE 16

Discrimination of cocaine from saline to demonstrate the stability and reliability of the rat cocaine model To demonstrate the stability and reproducibility of this system, 8 rats are trained to discriminate i.p. injections of 10 mg/kg cocaine from saline using a 2-lever procedure (Kantak et al., J. Pharmacol. Exp. Therap. (1994)). After cocaine injections are given by the experimenter, the animals are required to press one of the levers (drug-appropriate lever) 10 times (FR 10) to obtain a food pellet; upon saline injections, they are required to press the other lever (saline-appropriate lever) 10 times to obtain a food pellet. When animals have learned to discriminate cocaine from saline, at least 90% of the total responses are made on the appropriate lever for several consecutive days. In order to incorporate a cumulative dosing procedure during later substitution test sessions, training sessions are made up of multiple components, each lasting for 10 min or until 10 FRs are completed, whichever occurred first.

Following training, substitution test sessions with different doses of cocaine (0.3–17.8 mg/kg) are conducted twice weekly, with training sessions on intervening days. Drug substitution test sessions consisted of four 10 min components, each preceded by a 15 min time-out period. During substitution tests, completion of 10 responses on either lever produce a food pellet. Incremental doses of cocaine are injected at the beginning of each of the 4 time-out periods. Overlapping ranges of cumulative doses are studied on different test days, permitting a seven-point cumulative dose-response curve to be determined in a single week.

In substitution tests, cocaine engendered dose-related increases in the percentage of cocaine-appropriate responses, which result in full substitution (>90% cocaine-appropriate responses) for all subjects after administration of doses that are at least the level of the training dose. Each data point is based on 2–3 determinations in individual subjects. The $ED_{50}\pm95\%$ C.I. for cocaine-appropriate responses is 2.14±0.20 mg/kg, which compares favorably to the value obtained in rats trained to discriminate injections of 10 mg/kg cocaine using single component and single dosing procedures (2.6±0.29 mg/kg; (25)).

EXAMPLE 17

Figure 12C:
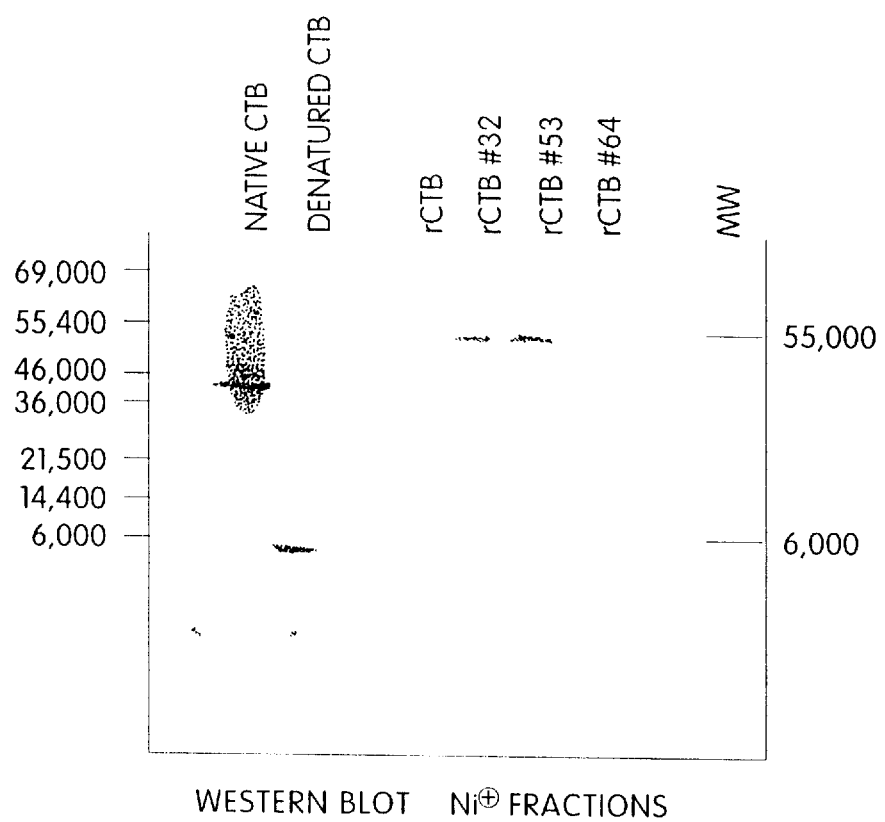
FIG. 12C shows a drawing of an actual Western Blot gel showing peak fractions rCTB#32 and rCTB#53 which were obtained by periplasmic expression resulting in pentameric CTB.
Figure 14A:
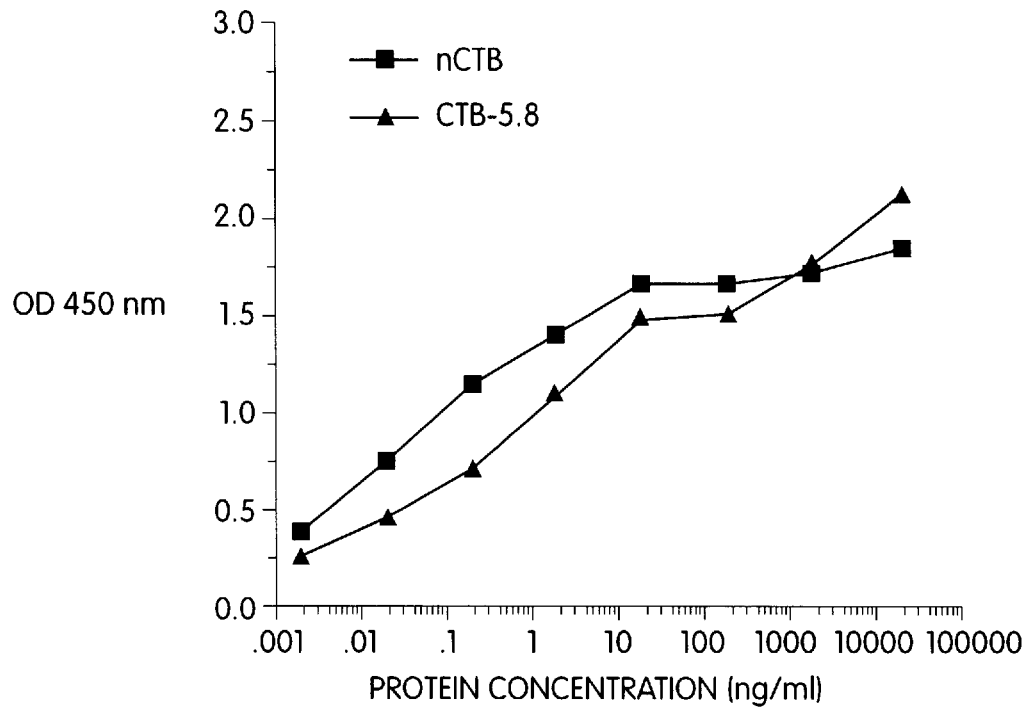
FIG. 14A and 14B demonstrate a cocaine-CTB conjugate retains its pentameric structure and expresses detectable quantities of cocaine.
Figure 14B:
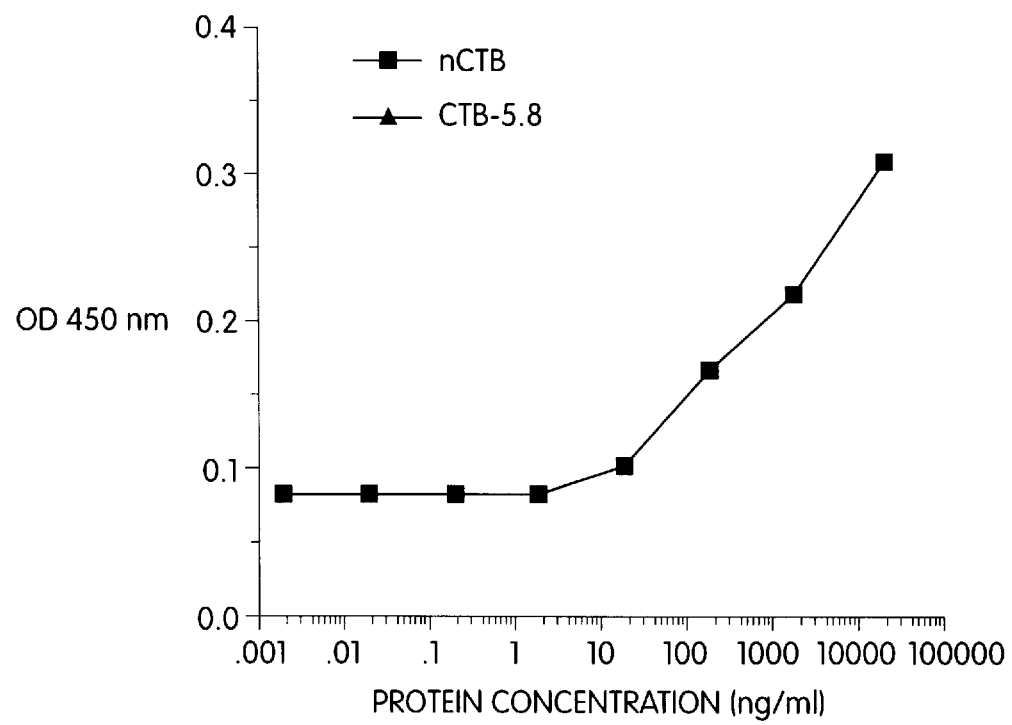

Assays to detect the function activity of CTB,

To test the functional activity of CTB alone, two assays were developed. First, binding of CTB to cells was measured using flow cytometry. Cells were incubated with CTB, followed by a commercial anti-CTB goat antiserum and a FITC-labeled anti-goat secondary antibody. (FIGS. 12, 13 and 14) Native pentameric CTB bound to the cells, causing a dramatic shift in fluorescence intensity. Monomeric CTB was unable to bind to cells in this assay. Second, an ELISA was set up to measure the ability of the CTB to bind to ganglioside $G_{M1}$. ELISA plates were coated with $G_{M1}$-ganglioside and incubated with varying concentrations of CTB. Binding was detected using an anti-CTB antibody (or saline as a control) followed by enzyme-labeled second antibody and development with substrate. This assay provided a quantitative and extremely sensitive measure of the ability of pentameric CTB to bind to $G_{M1}$ gangliosides. These assays are used to monitor the functional activity of recombinant and haptenated CTB conjugates prior to experiments in vivo.

EXAMPLE 18

Self-administration model of addiction and effect of vaccine

In rats, the reinforcing stimulus properties of cocaine can be studied reliably using intravenous self-administration procedures. This is a direct model of addiction and drug self-administration behavior in animal subjects positively correlates with abuse of that drug by human subjects. To examine the effect of the therapeutic vaccine, adult male rats (Wistar, approximately 300 g) are implanted with a chronic jugular vein catheter using the general procedures described by Weeks (Weeks, *Methods in Psychobiology*, vol. 2, 1972, 115–168 and as adapted by Kantak et al. (Kantak et a., *Pharm Biochem, & Behavior*, vol. 36, 1990,9–12), (Kantak et al., *Psychopharm.*, 104:527–535 (1991)) and (Kantak et al., *Pharmacol. of Biochem. and Behavior*, 41:415–423 (1992)). All animals are housed individually and maintained at 80%–85% of their free feeding body weights to facilitate comparison with the drug discrimination experiments. One week following surgery, 1.0 mg/kg/infusion of cocaine is available as the training dose in daily 2 hr sessions. Rats typically self-infuse a cumulative dose of 10 mg/kg each hour. During the initial phase of training, each lever press results in drug delivery. The required number of responses to self-infuse cocaine is increased gradually to 5 (FR 5) and then the FR 5:FI 5 min schedule of drug delivery is introduced. Following stable responding for at least 5 days, a baseline cocaine dose-response curve (0.1, 0.3, 0.56, 1.0 and 3.0 mg/kg/infusion) is determined. Each dose of cocaine, as well as saline, is examined for a block of at least 5 sessions and until no systematic upward or downward trends in responding are observed. Data is expressed as mean response rates over the last two days of each block of sessions.

Following determination of the baseline cocaine dose-response curve in 30 rats, half the rats are immunized with the optimal cocaine-carrier conjugate and the other half are immunized with carrier alone. Self-administration sessions are discontinued until significant anti-cocaine antibody titers are achieved, which should take 4–6 weeks. Rats are bled from the tail vein to ensure that all rats have comparable titers of cocaine-specific antibodies. Following immunization, the rats are tested for their ability to respond to cocaine. Rats will have access to varying doses of cocaine (0.3–3.0 mg/kg/infusion), or to saline, in 5-day blocks. Control rats immunized with carrier alone quickly return to the baseline pattern of cocaine self-administration.

Anti-cocaine antibody blocks the reinforcing effects of cocaine. If necessary, doses of cocaine up to 30 mg/kg/infusion are examined to determine how much protection the antibody affords. If the anti-cocaine antibody partially blocks cocaine, the rats require much larger doses of cocaine to achieve the desired physiological effect and responses maintained by cocaine are reinstated with a rightward shift in the cocaine dose-response curve. If the polyclonal cocaine antibody completely blocks doses of cocaine up to 30 mg/kg/infusion, then responding which is maintained by cocaine is not be reinstated and cocaine self-administration extinguishes, with the cocaine dose-response curve remaining flat at near-zero saline-like levels.

EXAMPLE 19

Co-treatment with other drugs.

Screening is done to determine whether pharmacotherapy with buprenorphine and/or desipramine will enhance the activity of the therapeutic vaccine. Treatment with buprenorphine and/or desipramine are expected to be compatible. Incompatibility, if any, could arise if the anti-cocaine antibody induced by the cocaine-CTB conjugate recognizes the therapeutic agents and thus block their activity. However, it is believed unlikely because of the unrelated structures. In addition, it is possible that the therapeutic agents could be immunosuppressive, thus inhibiting the induction of a high titer anti-cocaine antibody response. To address this possibility, rats are immunized with the cocaine-carrier conjugate in the presence or absence of buprenorphine or desipramine and the antibody titer is measured at varying times. It is much less time consuming and more efficient to measure immunosuppression measuring antibody titer rather than behavior. A drug is found to be significantly immunosuppressive will be eliminated as an incompatible therapy. This screening test is used for any drug for which co-treatment is considered.

If no immunosuppression is seen, further screening is carried out to determine if the two approaches synergize. Following training, immunization and testing, rats are further evaluated in the two models in the presence of the drugs. Rats will receive drugs before sessions with different doses of cocaine. Initial experiments with control carrier-immunized rats are performed to choose a dose of drug that does not completely extinguish behavior in the self-administration or drug discrimination systems; it is estimated that this dose is approximately 5.6 mg/kg (−)-buprenorphine or 10 mg/kg desipramine. Data is evaluated to determine whether the action of the therapeutic vaccine is additive with the treatment with buprenorphine or desipramine.

EXAMPLE 20

Induction of mucosal response

As mentioned earlier, cholera toxin is an appealing reagent for the induction of a mucosal response, as it functions both as an adjuvant and as a powerful carrier molecule. The B subunit of cholera toxin, CTB, has been shown in many systems to retain the activity of intact cholera toxin, including the induction of a mucosal antibody response. Therefore, this carrier should induce a strong anti-cocaine IgA antibody response.

One effective way to prime an immune response in the respiratory tract, the antigen is delivered directly to those sites. The antigen is administered in saline, with CTB acting as its own adjuvant. To confirm the ability of CTB to prime a mucosal IgA response, initial experiments are conducted with carrier alone. If CTB fails to induce a mucosal anti-CTB response, other carriers will be evaluated prior to scale-up of the cocaine-carrier conjugate. Mice are primed with 50 µg of the CTB or cocaine-CTB conjugate by two routes: nasally or intratracheally. Nasal administration is a simple and common route of priming. Antigen is applied to each nostril of a lightly anesthetized mouse, for a total volume of 50 µl per mouse. Fourteen days after priming, the mice are boosted using the same protocol. Nasal administration is adaptable readily to human application as a nasal spray. Nasal vaccination has been used successfully with live influenza vaccines (Walker et al., Vaccine, 12:387–399 (1994)).

Intratracheal immunization is technically more difficult and thus less widely used in experimental animals. However, it has the advantage that it directly applies the antigen to the lower respiratory tract, which enhances immunity in the lungs. Murine intratracheal injections currently are being performed. Mice are anesthetized with a cocktail of ketamine and xylazine. The animals are mounted on an apparatus that holds their mouth open and exposes the trachea; the trachea is visualized with a fiberoptic light probe. A blunt 23 gauge needle is used to deliver 50 µl of solution into the lungs. Fourteen days after priming, the mice are boosted using the same protocol. Intratracheal immunization is not directly applicable to humans; however, a finding that this route of administration generated the most effective IgA response shows that a comparable route of administration should be developed, perhaps in the form of an inhalant.

Animals are sacrificed by $CO_2$ asphyxiation at varying time points after boost (14, 21, or 28 days) and nasal and bronchoalveolar lavage fluids are collected and assayed for IgA specific for the administered conjugate. Nasal wash fluid is obtained by washing the nasal cavity 4×with a total of 1 ml PBS as described (Tamura et al., Vaccine, 71, 1989). Bronchoalveolar lavage fluid is obtained by surgically exposing the trachea, injecting 0.5 ml PBS into the lungs, and rinsing 3×as described (Nedrud et al., J. Immunol., 139:3484–3492 (1987)). Following centrifugation to remove cells, samples are assayed for antigen-specific IgA by ELISA using an IgA-specific second antibody. Cocaine-specific IgG is measured in the nasal and lung washes, as it has been reported that IgG is frequently both detectable and important in the lung (Cahill et al., FEMS Microbiology Letters, 107:211–216 (1993)).

The two routes of administration are compared directly for their ability to induce an IgA response in both the lung or nasal lavage fluid. Whichever route is found to be most potent, it is preferred and used for the remaining experiments. If the two routes are of comparable efficacy, nasal immunization is preferred because of its simplicity.

For maximal protection against cocaine, it would be best to maximize both systemic IgG and mucosal IgA responses. Therefore, both a systemic injection with the cocaine-CTB conjugate in alum (or some other adjuvant) and a mucosal challenge with the conjugate are preferred to effectively prime both compartments. Three groups are compared. First, mice are primed systemically, followed by a mucosal challenge after 14 days. Second, the mice are primed mucosally, followed by a systemic challenge after 14 days. Third, they are primed both systemically and mucosally at the same time, followed by an identical boost after 14 days. Control mice are primed only mucosally or only systemically. In each case, efficacy in challenge is determined by measurement of both IgG and IgA anti-cocaine antibody titers.

As an initial measure of the in vivo efficacy of mucosal anti-cocaine antibodies, the LD50 is measured for mucosally administered cocaine. Varying doses of cocaine are administered to anesthetized mice either intratracheally or intranasally. Three groups of mice are compared in the $LD_{50}$ experiment: naive mice, mice which only have been immunized systemically and mice which have been immunized both systemically and mucosally. The actual $LD_{50}$ of all groups may be shifted by anesthetization (TelIa et al., Journal of Pharm. & Exper. Therap., 262:936–946 (1992)). If these data prove promising, evaluation of the approach in a non-human primate model of cocaine using smoked cocaine base is to be pursued (Carroll et al., Journal of Pharm. and Exper. Therap., 261:26–37 (1992)).

EXAMPLE 21

Direct binding of cocaine by antibodies from immunized mice

The ability of the antibodies to bind free cocaine can be assessed using radiolabeled cocaine. [$^3$H]Cocaine (1 µCi) was incubated with serum from normal mice (0.05 ml), with serum from mice immunized with a PS-5 (conjugated with BSA) (0.05 ml, pool of serum from 10 mice) or with commercially available anti-cocaine monoclonal antibodies (mixture of two different antibodies, 2 µg of each). See FIG. 10A. Beads coated with protein G were included in the incubation to bind to the Fc portion of antibody molecules. After 2 hours, the beads were pelleted by centrifugation, washed three times with cold PBS and counted in a scintillation counter. The data on FIG. 10B represent the mean and standard deviations of duplicate samples. These data clearly show that the immune serum is able to bind free cocaine with an affinity sufficiently high to permit the bound cocaine to be precipitated and washed. This is evidence that these antibodies will be able to bind and neutralize cocaine in the circulation of cocaine addicts.

What is claimed is:

1. A method of treating drug addiction to cocaine in mammals comprising
   (a) providing a therapeutic composition comprising at least one conjugate of a hapten-carrier conjugate selected from the group consisting of PS-2, PS-4, PS-5 and PS-6 all as shown in FIG. 3a wherein Q in FIG. 3a is a carrier comprising at least one T-cell epitope, and a pharmaceutically acceptable carrier, said conjugate being capable of stimulating the production of anti-drug antibodies.
   (b) administering said therapeutic composition to a subject mammal,
   (c) measuring titer of anti-drug antibodies,
   (d) monitoring said subject mammal for a desired therapeutic effect wherein a sustainable increase of sufficiently high titer of anti-drug antibodies indicates a desired measurable outcome.

2. A method of treating drug addiction to cocaine in mammals comprising administering a therapeutically effective amount of a composition to a mammal in need of treatment for drug addiction, said composition comprised of at least one hapten-carrier conjugate selected from the group consisting of PS-2, PS-4, PS-5 and PS-6 as shown in FIG. 3a wherein Q in FIG. 3a is a carrier comprising at least one T cell epitope; and a pharmaceutically acceptable carrier.

3. A method for treating drug addiction in a mammal comprising passive immunization of said mammal with an intact antibody specific for the hapten component of a hapten-carrier conjugate selected from the group consisting of PS-2, PS-4, PS-5 and PS-6 all as shown in FIG. 3a wherein Q in FIG. 3a is a carrier comprising at least one T cell epitope, and a pharmaceutically acceptable carrier.

* * * * *